United States Patent
Grenon et al.

(10) Patent No.: US 10,940,074 B2
(45) Date of Patent: Mar. 9, 2021

(54) MELTING MEIBOMIAN GLAND OBSTRUCTIONS

(71) Applicant: TearScience, Inc., Morrisville, NC (US)

(72) Inventors: Stephen M. Grenon, Durham, NC (US); Omer Jack Barrier, Raleigh, NC (US); David Foshee, Apex, NC (US); Donald R. Korb, Boston, MA (US); Timothy R. Willis, Raleigh, NC (US)

(73) Assignee: TearScience Inc, Morrisville, NC (US)

( * ) Notice: Subject to any disclaimer, the term of this patent is extended or adjusted under 35 U.S.C. 154(b) by 86 days.

(21) Appl. No.: 16/172,159

(22) Filed: Oct. 26, 2018

(65) Prior Publication Data

US 2019/0060158 A1    Feb. 28, 2019

Related U.S. Application Data

(60) Division of application No. 11/541,308, filed on Sep. 29, 2006, now abandoned, which is a (Continued)

(51) Int. Cl.
*A61H 7/00* (2006.01)
*A61F 9/00* (2006.01)
(Continued)

(52) U.S. Cl.
CPC ............... *A61H 7/001* (2013.01); *A61F 9/00* (2013.01); *A61F 9/00772* (2013.01); *A61H 7/00* (2013.01);
(Continued)

(58) Field of Classification Search
CPC .... A61H 7/001; A61H 7/00; A61H 2205/024; A61H 2205/022; A61H 2201/165;
(Continued)

(56) References Cited

U.S. PATENT DOCUMENTS

| 168,352 A | 10/1875 | Sloan |
|---|---|---|
| 1,006,945 A | 10/1911 | Houston |

(Continued)

FOREIGN PATENT DOCUMENTS

| AU | 2011203832 A1 | 8/2012 |
|---|---|---|
| AU | 2011302478 A1 | 3/2013 |

(Continued)

OTHER PUBLICATIONS

Non-final Office Action for U.S. Appl. No. 13/368,976 dated Aug. 31, 2012, 10 pages.

(Continued)

*Primary Examiner* — Gary Jackson
*Assistant Examiner* — Sebastian X Lukjan

(57) ABSTRACT

An apparatus providing heat for treatment of an eyelid includes a heater unit configured to apply heat directly to an outer surface of the eyelid when an electrical signal is applied to the heater unit. The heater unit is affixed directly to the outer surface of the eyelid using an adhesive. A temperature regulator applies the electrical signal to the heater unit in order to achieve heating of the outer surface of the eyelid to a specified temperature range. A method is also disclosed that comprises affixing a heater unit directly into contact with the outer surface of the eyelid using an the adhesive. A control signal is applied to the heater unit to generate heat to the outer surface of the eyelid and is maintained for a period of time until the outer surface of the eyelid is heated to a specified temperature range.

16 Claims, 13 Drawing Sheets

Related U.S. Application Data continuation-in-part of application No. 11/434,054, filed on May 15, 2006, now Pat. No. 8,083,787.

(60) Provisional application No. 60/700,233, filed on Jul. 18, 2005.

(51) Int. Cl.
| | |
|---|---|
| A61F 9/007 | (2006.01) |
| A61B 18/12 | (2006.01) |
| A61B 18/04 | (2006.01) |
| A61F 7/00 | (2006.01) |
| A61H 15/00 | (2006.01) |
| A61N 7/00 | (2006.01) |

(52) U.S. Cl.
CPC .......... *A61B 18/12* (2013.01); *A61B 2018/046* (2013.01); *A61B 2018/048* (2013.01); *A61F 2007/0004* (2013.01); *A61F 2007/0059* (2013.01); *A61H 2015/0014* (2013.01); *A61H 2201/0207* (2013.01); *A61H 2201/0221* (2013.01); *A61H 2201/1604* (2013.01); *A61H 2201/165* (2013.01); *A61H 2205/022* (2013.01); *A61H 2205/024* (2013.01); *A61N 7/00* (2013.01)

(58) Field of Classification Search
CPC .... A61H 2201/1604; A61H 2201/0207; A61H 2015/0014; A61F 9/00772; A61F 9/00; A61F 2007/0059; A61F 2007/0004; A61N 7/00; A51H 2201/0221; A61B 2018/048; A61B 2018/046; A61B 18/12
See application file for complete search history.

(56) References Cited

U.S. PATENT DOCUMENTS

| | | | |
|---|---|---|---|
| 1,924,315 A | 8/1933 | Hemphill et al. | |
| 2,545,724 A | 3/1951 | Curtis | |
| 2,891,252 A | 6/1959 | Lazo | |
| 3,140,390 A | 7/1964 | Smith et al. | |
| 3,173,419 A | 3/1965 | Dubilier et al. | |
| 3,333,586 A | 8/1967 | Bellis et al. | |
| 3,404,678 A | 10/1968 | Von Ardenne | |
| 3,415,299 A | 12/1968 | Hinman, Jr. et al. | |
| 3,667,476 A | 6/1972 | Muller | |
| 3,915,346 A | 10/1975 | Allsop | |
| 3,952,735 A | 4/1976 | Wirtschafter et al. | |
| 4,069,084 A | 1/1978 | Mlodozeniec et al. | |
| 4,131,115 A | 12/1978 | Peng | |
| 4,261,364 A * | 4/1981 | Haddad ............... | A61F 7/007 219/528 |
| 4,387,707 A | 6/1983 | Polikoff | |
| 4,612,959 A | 9/1986 | Costello | |
| 4,778,457 A | 10/1988 | York | |
| 4,883,454 A | 11/1989 | Hamburg | |
| 4,914,088 A | 4/1990 | Glonek et al. | |
| 4,918,818 A | 4/1990 | Hsieh | |
| 4,955,377 A | 9/1990 | Lennox et al. | |
| 4,958,632 A | 9/1990 | Duggan | |
| 5,020,455 A | 6/1991 | Takashi et al. | |
| 5,030,214 A | 7/1991 | Spector | |
| 5,097,829 A | 3/1992 | Quisenberry | |
| 5,151,100 A | 9/1992 | Abele et al. | |
| 5,158,082 A | 10/1992 | Jones | |
| 5,169,384 A * | 12/1992 | Bosniak ............... | A61N 1/044 604/20 |
| 5,213,097 A | 5/1993 | Zeindler | |
| 5,251,627 A | 10/1993 | Morris | |
| 5,283,063 A | 2/1994 | Freeman | |
| 5,314,456 A | 5/1994 | Cohen | |
| 5,327,886 A | 7/1994 | Chiu | |
| 5,343,561 A | 9/1994 | Adamo | |
| D352,106 S | 11/1994 | Fanney et al. | |
| 5,368,582 A | 11/1994 | Bertera | |
| 5,368,591 A | 11/1994 | Lennox et al. | |
| 5,377,701 A | 1/1995 | Fang | |
| 5,419,772 A | 5/1995 | Teitz et al. | |
| 5,425,380 A | 6/1995 | Hudson et al. | |
| 5,496,311 A | 3/1996 | Abele et al. | |
| 5,601,548 A | 2/1997 | Smith et al. | |
| 5,628,772 A | 5/1997 | Russell | |
| 5,643,336 A | 7/1997 | Lopez-Claros | |
| 5,700,238 A | 12/1997 | Hyson | |
| 5,720,773 A | 2/1998 | Lopez-Claros | |
| 5,769,806 A | 6/1998 | Radow | |
| 5,782,857 A | 7/1998 | Machuron | |
| 5,795,312 A | 8/1998 | Dye | |
| 5,807,357 A | 9/1998 | Kang | |
| 5,836,927 A | 11/1998 | Fried | |
| 5,893,719 A | 4/1999 | Radow | |
| 5,958,912 A | 9/1999 | Sullivan | |
| 5,960,608 A | 10/1999 | Ohtonen | |
| 5,964,723 A | 10/1999 | Augustine | |
| 6,007,501 A | 12/1999 | Cabados et al. | |
| 6,024,095 A | 2/2000 | Stanley, III | |
| 6,041,821 A | 3/2000 | Grossman | |
| 6,090,060 A | 7/2000 | Radow | |
| 6,095,992 A * | 8/2000 | Augustine ............... | A61F 7/007 602/14 |
| 6,107,289 A | 8/2000 | Sullivan | |
| 6,110,292 A | 8/2000 | Jewett et al. | |
| 6,112,900 A | 9/2000 | Adkins, Jr. | |
| 6,113,561 A | 9/2000 | Augustine | |
| 6,153,607 A | 11/2000 | Pflugfelder et al. | |
| 6,155,995 A | 12/2000 | Lin | |
| 6,181,970 B1 | 1/2001 | Kasevich | |
| 6,193,740 B1 | 2/2001 | Rodriguez | |
| 6,206,842 B1 | 3/2001 | Tu et al. | |
| 6,213,966 B1 | 4/2001 | Augustine | |
| 6,273,886 B1 | 8/2001 | Edwards et al. | |
| 6,275,735 B1 | 8/2001 | Jarding et al. | |
| 6,302,901 B1 * | 10/2001 | Lu ........................... | A61F 7/007 607/100 |
| 6,309,364 B1 | 10/2001 | Cathaud et al. | |
| 6,312,397 B1 | 11/2001 | Gebhard | |
| D456,079 S | 4/2002 | Fujii | |
| 6,423,018 B1 | 7/2002 | Augustine | |
| 6,425,888 B1 | 7/2002 | Embleton et al. | |
| 6,436,128 B1 | 8/2002 | Usui | |
| 6,438,398 B1 | 8/2002 | Pflugfelder et al. | |
| 6,455,583 B1 | 9/2002 | Pflugfelder et al. | |
| 6,482,203 B2 | 11/2002 | Paddock et al. | |
| 6,490,488 B1 | 12/2002 | Rudie et al. | |
| D472,637 S | 4/2003 | Cooper et al. | |
| 6,544,193 B2 | 4/2003 | Abreu | |
| 6,544,257 B2 | 4/2003 | Nagase et al. | |
| 6,569,189 B1 | 5/2003 | Augustine et al. | |
| D477,084 S | 7/2003 | Menezes et al. | |
| 6,641,264 B1 | 11/2003 | Schwebel | |
| 6,648,904 B2 | 11/2003 | Altshuler et al. | |
| 6,706,001 B2 | 3/2004 | Fresco | |
| 6,780,176 B2 | 8/2004 | Hasegawa | |
| 6,788,977 B2 | 9/2004 | Fenn et al. | |
| 6,827,898 B1 | 12/2004 | Fausset et al. | |
| 6,840,954 B2 | 1/2005 | Dietz et al. | |
| 6,860,852 B2 | 3/2005 | Schonenberger et al. | |
| 6,860,880 B2 | 3/2005 | Treat et al. | |
| 6,874,884 B2 | 4/2005 | Schwebel | |
| 6,882,885 B2 | 4/2005 | Levy, Jr. et al. | |
| 6,886,933 B2 | 5/2005 | Schwebel | |
| 6,908,195 B2 | 6/2005 | Fuller | |
| 6,925,317 B1 | 8/2005 | Samuels et al. | |
| 6,974,454 B2 | 12/2005 | Hooven | |
| 7,001,379 B2 | 2/2006 | Behl et al. | |
| 7,004,942 B2 | 2/2006 | Laird et al. | |
| 7,036,928 B2 | 5/2006 | Schwebel | |
| 7,060,061 B2 | 6/2006 | Altshuler et al. | |
| 7,069,084 B2 | 6/2006 | Yee | |
| 7,108,694 B2 | 9/2006 | Miura et al. | |
| 7,118,591 B2 | 10/2006 | Frank et al. | |
| 7,122,013 B2 | 10/2006 | Liu | |

(56) References Cited

U.S. PATENT DOCUMENTS

| | | | |
|---|---|---|---|
| 7,122,029 B2 * | 10/2006 | Koop | A61B 18/20 606/9 |
| 7,122,047 B2 | 10/2006 | Grahn et al. | |
| 7,123,968 B1 | 10/2006 | Casscells, III et al. | |
| 7,211,070 B2 | 5/2007 | Soroudi | |
| 7,229,468 B2 | 6/2007 | Wong et al. | |
| 7,231,922 B2 | 6/2007 | Davison et al. | |
| D546,459 S | 7/2007 | Banryu | |
| D552,736 S | 10/2007 | Yamaoka | |
| D553,750 S | 10/2007 | Yamaoka | |
| 7,316,657 B2 | 1/2008 | Kleinhenz et al. | |
| 7,357,500 B2 | 4/2008 | Schwebel | |
| 7,384,405 B2 | 6/2008 | Rhoades | |
| 7,442,174 B2 | 10/2008 | Butler | |
| 7,513,893 B2 | 4/2009 | Soroudi | |
| 7,559,907 B2 | 7/2009 | Krempel et al. | |
| 7,594,728 B2 | 9/2009 | Seal et al. | |
| 7,637,878 B2 | 12/2009 | Lin | |
| D612,941 S | 3/2010 | Youngquist et al. | |
| D614,774 S | 4/2010 | Gausmann et al. | |
| 7,712,899 B2 | 5/2010 | Tanassi et al. | |
| 7,976,573 B2 | 7/2011 | Korb et al. | |
| 7,981,095 B2 | 7/2011 | Grenon et al. | |
| 7,981,145 B2 | 7/2011 | Korb et al. | |
| 7,981,146 B2 | 7/2011 | Korb et al. | |
| 7,981,147 B2 | 7/2011 | Korb et al. | |
| 8,007,524 B2 | 8/2011 | Korb et al. | |
| D645,565 S | 9/2011 | Smith et al. | |
| 8,025,689 B2 | 9/2011 | Korb et al. | |
| 8,083,787 B2 | 12/2011 | Korb et al. | |
| 8,128,673 B2 | 3/2012 | Korb et al. | |
| 8,128,674 B2 | 3/2012 | Korb et al. | |
| 8,137,390 B2 | 3/2012 | Korb et al. | |
| 8,187,310 B2 | 5/2012 | Korb et al. | |
| 8,255,039 B2 | 8/2012 | Gravely et al. | |
| 8,262,715 B2 | 9/2012 | Wong, Jr. et al. | |
| 8,455,016 B2 | 6/2013 | Maskin | |
| 8,491,508 B2 | 7/2013 | Smith et al. | |
| 8,617,229 B2 | 12/2013 | Korb et al. | |
| 8,628,504 B2 | 1/2014 | Grenon et al. | |
| 8,791,158 B2 | 7/2014 | Dalton et al. | |
| 8,906,427 B2 | 12/2014 | Maskin | |
| 8,915,253 B2 | 12/2014 | Grenon et al. | |
| 8,925,484 B2 | 1/2015 | Maier, Jr. et al. | |
| 8,950,405 B2 | 2/2015 | Grenon et al. | |
| 9,039,718 B2 | 5/2015 | Rynerson | |
| 9,060,843 B2 | 6/2015 | Grenon et al. | |
| 9,216,028 B2 | 12/2015 | Korb et al. | |
| 9,314,369 B2 | 4/2016 | Grenon et al. | |
| 9,510,972 B2 | 12/2016 | Badawi | |
| 9,719,977 B2 | 8/2017 | Korb et al. | |
| 9,763,827 B2 | 9/2017 | Kelleher et al. | |
| 9,822,142 B2 | 11/2017 | Cavanagh et al. | |
| 9,913,678 B2 | 3/2018 | Friedland et al. | |
| 2001/0039442 A1 | 11/2001 | Gorge et al. | |
| 2001/0041886 A1 | 11/2001 | Durkin et al. | |
| 2002/0013572 A1 | 1/2002 | Berlin | |
| 2002/0035345 A1 | 3/2002 | Beck | |
| 2002/0049374 A1 | 4/2002 | Abreu | |
| 2002/0099094 A1 | 7/2002 | Anderson | |
| 2002/0111608 A1 | 8/2002 | Baerveldt et al. | |
| 2002/0128696 A1 | 9/2002 | Pearl et al. | |
| 2002/0156402 A1 | 10/2002 | Woog et al. | |
| 2003/0050594 A1 | 3/2003 | Zamierowski | |
| 2003/0056281 A1 | 3/2003 | Hasegawa | |
| 2003/0065277 A1 | 4/2003 | Covington | |
| 2003/0073987 A1 | 4/2003 | Sakurai et al. | |
| 2003/0088241 A1 | 5/2003 | Hasegawa | |
| 2003/0100936 A1 | 5/2003 | Altshuler et al. | |
| 2003/0114426 A1 | 6/2003 | Pflugfelder et al. | |
| 2003/0139790 A1 | 7/2003 | Ingle et al. | |
| 2003/0195438 A1 | 10/2003 | Petillo | |
| 2003/0211043 A1 | 11/2003 | Korb | |
| 2003/0233135 A1 | 12/2003 | Yee | |
| 2004/0064169 A1 | 4/2004 | Briscoe et al. | |
| 2004/0064171 A1 | 4/2004 | Briscoe et al. | |
| 2004/0076695 A1 | 4/2004 | Gilbard | |
| 2004/0111138 A1 | 6/2004 | Bleam et al. | |
| 2004/0153093 A1 | 8/2004 | Donovan | |
| 2004/0199158 A1 | 10/2004 | Hood et al. | |
| 2004/0237696 A1 | 12/2004 | Hilsky et al. | |
| 2004/0237969 A1 * | 12/2004 | Fuller | A61H 35/02 128/858 |
| 2004/0249427 A1 | 12/2004 | Nabilsi | |
| 2004/0260209 A1 | 12/2004 | Ella et al. | |
| 2005/0022823 A1 | 2/2005 | Davison et al. | |
| 2005/0119629 A1 * | 6/2005 | Soroudi | A61F 9/0017 604/289 |
| 2005/0143798 A1 | 6/2005 | Bleam et al. | |
| 2005/0187502 A1 | 8/2005 | Krempel et al. | |
| 2005/0220742 A1 | 10/2005 | Breen | |
| 2005/0234506 A1 | 10/2005 | Weser | |
| 2006/0018953 A1 | 1/2006 | Guillon et al. | |
| 2006/0030604 A1 | 2/2006 | Elsinger et al. | |
| 2006/0055878 A1 | 3/2006 | Yee | |
| 2006/0069420 A1 | 3/2006 | Rademacher et al. | |
| 2006/0104914 A1 | 5/2006 | Soroudi | |
| 2006/0135890 A1 | 6/2006 | Tsai | |
| 2006/0136022 A1 * | 6/2006 | Wong, Jr. | A61B 5/6821 607/104 |
| 2006/0139569 A1 | 6/2006 | Schwebel | |
| 2006/0154901 A1 | 7/2006 | Pflugfelder et al. | |
| 2006/0157064 A1 | 7/2006 | Davison et al. | |
| 2006/0183698 A1 | 8/2006 | Abelson | |
| 2006/0212101 A1 | 9/2006 | Cheng | |
| 2006/0233859 A1 | 10/2006 | Whitcup et al. | |
| 2007/0016254 A1 | 1/2007 | Grenon et al. | |
| 2007/0016256 A1 | 1/2007 | Korb et al. | |
| 2007/0027411 A1 | 2/2007 | Ella et al. | |
| 2007/0027431 A1 | 2/2007 | Korb et al. | |
| 2007/0049913 A1 | 3/2007 | Grenon et al. | |
| 2007/0060988 A1 | 3/2007 | Grenon et al. | |
| 2007/0106349 A1 | 5/2007 | Karni et al. | |
| 2007/0129711 A1 | 6/2007 | Altshuler et al. | |
| 2007/0173799 A1 | 7/2007 | Hsia | |
| 2007/0203462 A1 | 8/2007 | Soroudi | |
| 2007/0270760 A1 | 11/2007 | Dacquay et al. | |
| 2007/0280924 A1 | 12/2007 | Daniels et al. | |
| 2008/0051741 A1 | 2/2008 | Grenon et al. | |
| 2008/0075787 A1 | 3/2008 | Hibino | |
| 2008/0081999 A1 | 4/2008 | Gravely et al. | |
| 2008/0109052 A1 | 5/2008 | Grenon et al. | |
| 2008/0109053 A1 | 5/2008 | Grenon et al. | |
| 2008/0114423 A1 | 5/2008 | Grenon et al. | |
| 2008/0132973 A1 | 6/2008 | Lord et al. | |
| 2008/0188839 A1 | 8/2008 | Chan et al. | |
| 2008/0200848 A1 | 8/2008 | Avni | |
| 2008/0221649 A1 | 9/2008 | Echague et al. | |
| 2008/0251085 A1 | 10/2008 | Schwebel | |
| 2009/0043365 A1 | 2/2009 | Friedland et al. | |
| 2009/0137533 A1 | 5/2009 | Adkins, Jr. | |
| 2009/0149930 A1 | 6/2009 | Schenck | |
| 2009/0192478 A1 | 7/2009 | Soroudi | |
| 2009/0306111 A1 | 12/2009 | Nakamura et al. | |
| 2009/0306607 A1 | 12/2009 | Yasuhiro | |
| 2010/0087899 A1 | 4/2010 | Erez et al. | |
| 2010/0100029 A1 | 4/2010 | Maskin | |
| 2010/0292630 A1 | 11/2010 | Maskin | |
| 2011/0022010 A1 | 1/2011 | Grenon et al. | |
| 2011/0039805 A1 | 2/2011 | Pflugfelder et al. | |
| 2011/0059902 A1 | 3/2011 | Sullivan et al. | |
| 2011/0059925 A1 | 3/2011 | Donnenfeld | |
| 2011/0124725 A1 | 5/2011 | Maskin | |
| 2011/0130729 A1 | 6/2011 | Korb et al. | |
| 2011/0172302 A1 | 7/2011 | Dalton et al. | |
| 2011/0203832 A1 | 8/2011 | Schrock | |
| 2011/0251532 A1 | 10/2011 | Yang | |
| 2011/0273550 A1 | 11/2011 | Amano et al. | |
| 2011/0294897 A1 | 12/2011 | Aberg et al. | |
| 2012/0003296 A1 | 1/2012 | Shantha et al. | |
| 2012/0016450 A1 | 1/2012 | Korb et al. | |
| 2012/0065556 A1 | 3/2012 | Smith et al. | |
| 2012/0093876 A1 | 4/2012 | Ousler, III et al. | |
| 2012/0109041 A1 | 5/2012 | Munz | |

(56) References Cited

U.S. PATENT DOCUMENTS

| | | |
|---|---|---|
| 2012/0128763 A1 | 5/2012 | Maskin |
| 2012/0209154 A1 | 8/2012 | Williams, III et al. |
| 2012/0220612 A1 | 8/2012 | Nakamura et al. |
| 2012/0321673 A1 | 12/2012 | Ogawa et al. |
| 2013/0045927 A1 | 2/2013 | Dana et al. |
| 2013/0046367 A1 | 2/2013 | Chen |
| 2013/0053733 A1 | 2/2013 | Korb et al. |
| 2013/0065867 A1 | 3/2013 | Smith et al. |
| 2013/0110101 A1 | 5/2013 | Van Valen et al. |
| 2013/0131171 A1 | 5/2013 | Maskin |
| 2013/0172790 A1 | 7/2013 | Badawi |
| 2013/0172829 A1 | 7/2013 | Badawi |
| 2014/0330129 A1 | 11/2014 | Grenon et al. |
| 2014/0378878 A1 | 12/2014 | Sharma et al. |
| 2015/0005750 A1 | 1/2015 | Kelleher et al. |
| 2015/0038851 A1 | 2/2015 | Hamrah et al. |
| 2015/0057701 A1 | 2/2015 | Kelleher et al. |
| 2015/0100001 A1 | 4/2015 | Bujak |
| 2015/0100063 A1 | 4/2015 | Korb et al. |
| 2015/0148711 A1 | 5/2015 | Bujak et al. |
| 2015/0174425 A1 | 6/2015 | Toyos et al. |
| 2015/0182415 A1 | 7/2015 | Olkowski et al. |
| 2015/0320590 A1 | 11/2015 | Whitehurst et al. |
| 2015/0320594 A1 | 11/2015 | Smith |
| 2016/0120692 A1 | 5/2016 | Chen |
| 2016/0120693 A1 | 5/2016 | Guillon et al. |
| 2016/0243116 A1 | 8/2016 | Jain et al. |
| 2016/0317379 A1 | 11/2016 | Mosaddegh |
| 2017/0014300 A1 | 1/2017 | Dippo et al. |
| 2017/0079834 A1 | 3/2017 | Badawi |
| 2017/0079842 A1 | 3/2017 | Maskin |
| 2019/0029878 A1 | 1/2019 | Linder et al. |

FOREIGN PATENT DOCUMENTS

| | | | |
|---|---|---|---|
| CA | 2331257 | A1 | 11/1999 |
| CA | 2679448 | A1 | 9/2008 |
| CA | 2787114 | A1 | 7/2011 |
| CA | 2809274 | A1 | 3/2012 |
| CN | 1297719 | A | 6/2001 |
| CN | 2650737 | Y | 10/2004 |
| CN | 1631344 | A | 6/2005 |
| CN | 1781466 | A | 6/2006 |
| CN | 2855388 | Y | 1/2007 |
| CN | 102204854 | A | 10/2011 |
| CN | 101663064 | B | 3/2013 |
| CN | 103002737 | A | 3/2013 |
| CN | 103108669 | A | 5/2013 |
| CN | 102600008 | B | 5/2014 |
| CN | 103816033 | A | 5/2014 |
| CN | 103948490 | A | 7/2014 |
| CN | 102697593 | B | 12/2014 |
| CN | 102697595 | B | 12/2014 |
| CN | 104203190 | A | 12/2014 |
| CN | 104398234 | A | 3/2015 |
| DE | 202005011496 | U1 | 7/2006 |
| EP | 1816980 | A2 | 8/2007 |
| EP | 2151438 | A1 | 2/2010 |
| EP | 1587468 | B1 | 1/2011 |
| EP | 2523556 | A1 | 11/2012 |
| JP | H0370557 | A | 3/1991 |
| JP | 06269473 | A | 9/1994 |
| JP | H06315499 | A | 11/1994 |
| JP | 10085248 | A | 4/1998 |
| JP | 11221247 | | 8/1999 |
| JP | 2000225141 | A | 8/2000 |
| JP | 2001276113 | A | 10/2001 |
| JP | 2002078727 | A | 3/2002 |
| JP | 2004350803 | A | 12/2004 |
| JP | U3112008 | B | 7/2005 |
| JP | 2005237724 | A | 9/2005 |
| JP | 2006198249 | A | 8/2006 |
| JP | 2010155012 | A | 7/2010 |
| JP | 2014205069 | A | 10/2014 |
| KR | 20120115380 | A | 10/2012 |
| KR | 101806298 | B1 | 12/2017 |
| MX | 2012008110 | A | 10/2012 |
| WO | 9810723 | A1 | 3/1998 |
| WO | 9920213 | A1 | 4/1999 |
| WO | 9958131 | A1 | 11/1999 |
| WO | 2004041134 | A1 | 5/2004 |
| WO | 2006058189 | A2 | 6/2006 |
| WO | 2006093851 | A2 | 9/2006 |
| WO | 2008024100 | A2 | 2/2008 |
| WO | 2008106228 | A2 | 9/2008 |
| WO | 2009064834 | A2 | 5/2009 |
| WO | 2010005527 | A1 | 1/2010 |
| WO | 2010056848 | A1 | 5/2010 |
| WO | 2011085385 | A1 | 7/2011 |
| WO | 2012036931 | A1 | 3/2012 |
| WO | 2012051313 | A2 | 4/2012 |
| WO | 2012137545 | A1 | 10/2012 |
| WO | 2013003594 | A3 | 1/2013 |
| WO | 2013003731 | A3 | 1/2013 |
| WO | 2013006574 | A1 | 1/2013 |
| WO | 2013036894 | A2 | 3/2013 |
| WO | 2013114127 | A1 | 8/2013 |
| WO | 2013126599 | A1 | 8/2013 |
| WO | 2013149318 | A1 | 10/2013 |
| WO | 2013166353 | A1 | 11/2013 |
| WO | 2014049841 | A1 | 4/2014 |
| WO | 2014158356 | A1 | 10/2014 |
| WO | 2014179356 | A1 | 11/2014 |
| WO | 2014179795 | A2 | 11/2014 |
| WO | 2015163821 | A1 | 10/2015 |
| WO | 2016070134 | A1 | 5/2016 |
| WO | 2017072575 | A1 | 5/2017 |
| WO | 2017100608 | A1 | 6/2017 |
| WO | 2017156002 | A1 | 9/2017 |
| WO | 2017178892 | A3 | 11/2017 |
| WO | 2018004234 | A1 | 1/2018 |

OTHER PUBLICATIONS

Non-final Office Action for U.S. Appl. No. 11/541,308 dated Aug. 31, 2012, 20 pages.

Non-final Office Action for U.S. Appl. No. 13/242,068 dated Aug. 29, 2012, 9 pages.

Non-final Office Action for U.S. Appl. No. 13/367,908 dated Sep. 13, 2012, 10 pages.

Second Office Action for Chinese patent application 201210077192.7 dated May 5, 2014, 3 pages.

Asbell, P. et al. "The international workshop on meibomian gland dysfunction: report of the clinical trials subcommittee," Investigative Ophthalmology and Visual Science, Mar. 2011, pp. 2065-2085.

Office Action for Japanese patent application 2009-546506 dated Sep. 4, 2012, 6 pages.

Foulks et al., "Improving awareness, identification, and management of meibomian gland dysfunction, " Ophthalmology, vol. 119, No. 10 Sup., Oct. 2012, 12 pages.

Arita, F. et al., "Comparison of the long-term effects of various topical antiglaucoma medications on meibomian glands," Cornea, vol. 31, No. 11, Nov. 2012, pp. 1229-1234.

Non-final Office Action for U.S. Appl. No. 11/931,398 dated Nov. 2, 2012, 8 pages.

Agnifili et al., "In vivo confocal microscopy of meibomian glands in glaucoma," British Journal of Ophthalmology, vol. 97, No. 3, Mar. 2013, pp. 343-349, United Kingdom.

Aragona, P. et al., "Towards a dynamic customised therapy for ocular surface dysfunctions," British Journal of Ophthalmology, vol. 97, No. 8, Aug. 13, pp. 955-960.

Arita, R. et al., "Topical diquafosol for patients with obstructive meibomian gland dysfunction," British Journal of Ophthalmology, vol. 97, No. 6, Jun. 2013, pp. 725-729.

Author Unknown, Definition of Platform, Merriam-Webster Dictionary, accessed Dec. 10, 2012, 3 pages, http://www.merriam-webster.com/dictionary/platform.

Author Unknown, Definition of On, Merriam-Webster Dictionary, accessed Dec. 14, 2012, 5 pages, http://www.merriam-webster.com/dictionary/on.

(56) References Cited

OTHER PUBLICATIONS

Author Unknown, Definition of Platform, Macmillan Dictionary, accessed Dec. 10, 2012, 2 pages, http://www.macmillandictionary.com/dictionary/british/platform.
Author Unknown, "New Breakthrough Treatment for Evaporative Dry Eye Disease Introduced by Dry Eye Specialist, Mark R. Mandel, M.D.," PR Newswire, Dec. 11, 2012, 2 pages, Hayward, California.
Cuevas, Miguel et al., "Correlations Among Symptoms, Signs, and Clinical Tests in Evaporative-Type Dry Eye Disease Caused by Meibomian Gland Dysfunction (MGD)," Current Eye Research, vol. 37, No. 10, Oct. 2012, pp. 855-863.
Greiner, J., "Long-term 12-month improvement in meibomian gland function and reduced dry eye symptoms with a single thermal pulsation treatment," Clinical and Experimental Ophthalmology, vol. 41, No. 6, Aug. 2013, pp. 524-530.
Her, Y. et al., "Dry eye and tear film functions in patients with psoriasis," Japanese Journal of Ophthalmology, vol. 57, No. 4, Jul. 2013, pp. 341-346.
Khandelwal, et al., "Androgen regulation of gene expression in human meibomian gland and conjunctival epithelial cells," Molecular Vision, vol. 18, Apr. 27, 2012, pp. 1055-1067.
Zhang et al., "Efficacy of physical therapy meibomian gland dysfunction," International Eye Science, International Journal of Ophthalmology, vol. 13, No. 6, Jun. 2013, pp. 1267-1268.
Li, Li-Hu et al., "Analysis of the efficacy in the treatment of meibomian gland dysfunction," International Eye Science, vol. 13, No. 7, Jul. 2013, pp. 1495-1497.
Lin, Hui et al., "Dry eye disease: A review of diagnostic approaches and treatments," Saudi Journal of Ophthalmology, vol. 28, Issue 3, Jul.-Sep. 2014, Saudi Ophthalmological Society, pp. 173-181.
Liu, Ze-Yuan et al., "Treatment of dry eye caused by meibomian gland dysfunction," International Eye Science, vol. 14, No. 2, Feb. 2014, pp. 270-272.
Lu, Hui et al., "Tear film measurement by optical reflectometry technique," Journal of Biomedical Optics, vol. 19, No. 2, Feb. 2014, 8 pages.
Ozer, P.A. et al., "Eyelid nodule in a child: a chalazion or idiopathic facial aseptic granuloma?" Eye, vol. 28, No. 9, Sep. 2014, The Royal College of Ophthalmologists, pp. 1146-1147.
Pucker, A. et al., "Analysis of Meibum and Tear Lipids," The Ocular Surface, vol. 10, No. 4, Oct. 2012, pp. 230-250.
Purslow, Christine, "Evaluation of the ocular tolerance of a novel eyelid-warming device used for meibomian gland dysfunction," Contact Lens & Anterior Eye, vol. 36, No. 5, Elsevier Ltd., Oct. 2013, pp. 226-231.
Suzuki, Tomo, "Meibomitis-Related Keratoconjunctivitis: Implications and Clinical Significance of Meibomian Gland Inflammation," Cornea, vol. 31, Supplemental Issue, Nov. 2012, pp. S41-S44.
Tang, Qin et al., "Clinical analysis of meibomian gland dysfunction in elderly patients," International Eye Science, vol. 13, No. 7, Jul. 2013, pp. 1419-1423.
Non-Final Rejection dated Dec. 27, 2012, for U.S. Appl. No. 12/015,593, 27 pages.
Final Office Action for U.S. Appl. No. 12/015,593 dated Oct. 3, 2013, 21 pages.
Non-final Office Action for U.S. Appl. No. 11/434,033 dated Feb. 19, 2014, 10 pages.
Final Office Action for U.S. Appl. No. 11/434,033 dated Jun. 2, 2014, 11 pages.
Notice of Allowance for U.S. Appl. No. 11/434,033 dated Aug. 8, 2014, 8 pages.
Final Office Action for U.S. Appl. No. 11/931,398 dated Mar. 4, 2013, 7 pages.
Advisory Action for U.S. Appl. No. 11/931,398 dated May 15, 2013, 2 pages.
Non-final Office Action for U.S. Appl. No. 11/931,398 dated Jun. 3, 2014, 8 pages.
Final Office Action for U.S. Appl. No. 11/541,308 dated Mar. 19, 2013, 25 pages.
Advisory Action for U.S. Appl. No. 11/541,308 dated Jun. 26, 2013, 3 pages.
Non-Final Rejection for U.S. Appl. No. 11/928,681, dated Nov. 20, 2012, 9 pages.
Non-Final Office Action for U.S. Appl. No. 13/183,901, dated Feb. 12, 2015, 9 pages.
Final Office Action for U.S. Appl. No. 11/928,681 dated Feb. 26, 2013, 7 pages.
Advisory Action for U.S. Appl. No. 11/928,681 dated May 3, 2013, 3 pages.
Non-final Office Action for U.S. Appl. No. 11/928,681 dated Jun. 4, 2014, 7 pages.
Notice of Allowance for U.S. Appl. No. 11/928,681, dated Sep. 22, 2014, 9 pages.
Non-final Office Action for U.S. Appl. No. 11/931,914 dated Jun. 10, 2014, 15 pages.
First Office Action for Chinese patent application 201210127347.3 dated Jan. 15, 2014, 13 pages.
International Preliminary Report on Patentability for International Patent Application No. PCT/US2007/000493, dated Mar. 5, 2009, 7 pages.
International Preliminary Report on Patentability for International Patent Application No. PCT/US2007/000525, dated Jul. 23, 2009, 8 pages.
International Preliminary Report on Patentability for PCT/US2007/000508 dated Mar. 5, 2009, 11 pages.
International Preliminary Report on Patentability for PCT/US2006/032544 dated Mar. 26, 2009, 5 pages.
Written Opinion for Brazilian Patent Application No. 0806635-3, dated Jul. 9, 2019, 9 pages.
Advisory Action for U.S. Appl. No. 14/746,328, dated Apr. 22, 2019, 3 pages.
First Office Action for Chinese Patent Application No. 201710219080.3, dated Mar. 14, 2019, 17 pages.
Notice of Allowance for U.S. Appl. No. 13/590,828, dated Mar. 8, 2017, 9 pages.
First Examination Report for Indian Patent Application No. 1318/MUMNP/2009, dated Mar. 14, 2017, 20 pages.
Final Office Action for U.S. Appl. No. 14/746,328, dated Nov. 16, 2017, 12 pages.
Final Office Action for U.S. Appl. No. 11/541,308, dated Oct. 25, 2017, 25 pages.
Notice of Allowance for U.S. Appl. No. 141074,123, dated Oct. 25, 2017, 8 pages.
Second Examination Report for Indian Patent Application No. 1318/MUMNP/2009, dated Nov. 18, 2017, 2 pages.
Advisory Action for U.S. Appl. No. 14/746,328, dated Mar. 5, 2018, 3 pages.
Non-Final Office Action for U.S. Appl. No. 14/746,328, dated Apr. 5, 2018, 21 pages.
Non-Final Office Action for U.S. Appl. No. 11/541,308, dated Mar. 21, 2018, 21 pages.
Non-Final Office Action for U.S. Appl. No. 14/510,863, dated Feb. 15, 2018, 14 pages.
Non-Final Office Action for U.S. Appl. No. 14/618,392, dated Mar. 15, 2018, 17 pages.
Final Office Action for U.S. Appl. No. 14/510,863, dated Sep. 26, 2018, 12 pages.
Restriction/Election Requirement for U.S. Appl. No. 11/434,033, dated Oct. 1, 2010, 5 pages.
Final Office Action for U.S. Appl. No. 11/541,308, dated Jul. 26, 2018, 22 pages.
Non-final Office Action for U.S. Appl. No. 13/367,865 dated Sep. 13, 2012, 9 pages.
Examination Report for European Patent Application No. 08727830.5 dated Oct. 5, 2015, 5 pages.
Extended European Search Report for European Patent Application No. 16170742.7, dated Sep. 8, 2016, 8 pages.
Fourth Office Action for Chinese Patent Application No. 201210127347.3, dated Feb. 29, 2016, 9 pages.
Decision of Rejection for Japanese Patent Application No. 2013-226709, dated Feb. 2, 2016, 8 pages.

(56) References Cited

OTHER PUBLICATIONS

Extended European Search Report for European Patent Application No. 18192086.9, dated Nov. 23, 2018, 8 pages.
Examination Report for European Patent Application No. 16170742.7, dated Dec. 7, 2018, 6 pages.
Written Opinion for Brazilian Patent Application No. 0806635-3, dated Dec. 18, 2018, 11 pages.
Notice of Allowance for U.S. Appl. No. 14/510,863, dated Dec. 19, 2018, 9 pages.
Final Office Action for U.S. Appl. No. 14/746,328, dated Jan. 2, 2019, 20 pages.
Tobler, David, et al., "Nanotech Silver Fights Microbes in Medical Devices," Medical Device and Diagnostic Industry, May 1, 2005, p. 164.
Toyos, Rolando, "Intense Pulsed Light for Dry Eye Syndrome," Cataract & Refractive Surgery Today, Apr. 2009, pp. 1-3.
Wolff, Eugene, "Eugene Wolff's Anatomy of the eye and orbit : including the central connexions, development, and comparative anatomy of the visual apparatus (book)," 1976, p. 170.
Unknown, "IFU Manual for PNT Model 1000—Rev H," Feb. 11, 2009, http://www.oi-pnt.com/files/IFU_Manual_Model_1000_English_with_Bargode_Rev_H.pdf, 24 pages.
Unknown, "TearScience Launches Breakthrough Technology in Canada to Address the Root Cause of Evaporative Dry Eye," Business Wire, Jun. 9, 2011, http://www.businesswire.com/news/home/20110609005860/en/TearScience-Launches-Breakthrough-Technology-Canada-Address-Root, 2 pages.
Vasta, Stephanie, "Aggressive Treatments Developed for Meibomian Gland Dysfunction," Primary Care Optometry News, Nov. 1, 2009, 3 pages.
Wang, Y. et al., "Baseline Profiles of Ocular Surface and Tear Dynamics After Allogeneic Hematopoietic Stem Cell Transplantation in Patients With or Without Chronic GVHD-Related Dry Eye," Bone Marrow Transplantation, vol. 45, No. 6, Jun. 2010, pp. 1077-1083.
Applicant-Initiated Interview Summary for U.S. Appl. No. 14/746,328, dated Mar. 4, 2019, 4 pages.
Korb, D. et al., "Meibomian gland therapeutic expression: quantifying the applied pressure and the limitation of resulting pain," Eye & Contact Lens, vol. 37 No. 5, Sep. 2011, pp. 298-301.
Akyol-Salman, I. et al., "Comparison of the efficacy of topical N-acetyl-cysteine and a topical steroid-antibiotic combination therapy in the treatment of meibomian gland dysfunction," Journal of Ocular Pharmacology and Therapeutics, vol. 28 No. 1, Feb. 2, 2012, pp. 49-52.
No Author, "TearScience's LipiFlow Multi-center Clinical Study Shows Improved Meibomian Gland Secretions and Dry Eye Symptoms," Business Wire, Mar. 5, 2012, 2 pages.
Non-Final Rejection for U.S. Appl. No. 11/434,033 dated Jan. 24, 2011, 7 pages.
Non-final Office Action for U.S. Appl. No. 11/434,033 dated Aug. 12, 2011, 8 pages.
Non-final Office Action for U.S. Appl. No. 11/931,398 dated Jan. 27, 2012, 4 pages.
Advisory Action for U.S. Appl. No. 11/434,446 dated Mar. 4, 2010, 2 pages.
Final Rejection for U.S. Appl. No. 11/434,446 dated Dec. 23, 2009, 16 pages.
Non-final Rejection for U.S. Appl. No. 11/434,446 dated Apr. 9, 2010, 17 pages.
Non-Final Rejection for U.S. Appl. No. 11/434,446 dated Jun. 17, 2009, 13 pages.
English translation of Official Action dated May 10, 2011, for Japanese Patent Application No. 2009-525529, 3 pages.
Notice of Allowance for U.S. Appl. No. 13/025,951 dated Mar. 28, 2012, 8 pages.
Non-final Office Action for U.S. Appl. No. 13/025,951 dated Oct. 25, 2011, 9 pages.
Notice of Allowance for U.S. Appl. No. 13/025,990 dated Mar. 28, 2012, 9 pages.
Non-final Office Action for U.S. Appl. No. 13/025,990 dated Oct. 25, 2011, 11 pages.
Notice of Allowance for U.S. Appl. No. 11/434,054 dated Oct. 18, 2011, 9 pages.
Non-final Office Action for U.S. Appl. No. 11/434,054 dated May 26, 2011, 7 pages.
Non-final Office Action for U.S. Appl. No. 11/434,054 dated Sep. 8, 2010, 7 pages.
Non-final Office Action for U.S. Appl. No. 11/434,054 dated Mar. 12, 2010, 7 pages.
Notice of Allowance for U.S. Appl. No. 12/821,183 dated Jul. 29, 2011, 8 pages.
Non-final Office Action for U.S. Appl. No. 12/821,183 dated May 26, 2011, 8 pages.
Non-final Office Action for U.S. Appl. No. 12/821,183 dated Dec. 21, 2010, 7 pages.
Notice of Allowance for U.S. Appl. No. 11/541,291 dated May 26, 2011, 7 pages.
Notice of Allowance for U.S. Appl. No. 11/541,291 dated Jan. 10, 2011, 6 pages.
Final Office Action for U.S. Appl. No. 11/541,291 dated Aug. 17, 2010, 6 pages.
Non-final Office Action for U.S. Appl. No. 11/541,291 dated Jun. 2, 2010, 10 pages.
Advisory Action for U.S. Appl. No. 11/541,291 dated Mar. 30, 2010, 3 pages.
Final Office Action for U.S. Appl. No. 11/541,291 dated Dec. 16, 2009, 11 pages.
Non-final Office Action for U.S. Appl. No. 11/541,291 dated May 19, 2009, 11 pages.
Notice of Allowance for U.S. Appl. No. 11/931,646 dated Aug. 5, 2010, 6 pages.
Advisory Action for U.S. Appl. No. 11/931,646 dated Mar. 30, 2010, 3 pages.
Final Office Action for U.S. Appl. No. 11/931,646 dated Dec. 15, 2009, 11 pages.
Non-final Office Action for U.S. Appl. No. 11/931,646 dated May 19, 2009, 11 pages.
Notice of Allowance for U.S. Appl. No. 11/541,418 dated May 26, 2011, 7 pages.
Advisory Action for U.S. Appl. No. 11/541,418 dated Apr. 6, 2011, 3 pages.
Final Office Action for U.S. Appl. No. 11/541,418 dated Mar. 10, 2011, 21 pages.
Non-final Office Action for U.S. Appl. No. 11/541,418 dated Jul. 12, 2010, 20 pages.
Notice of Allowance for U.S. Appl. No. 12/015,558 dated Jun. 1, 2011, 8 pages.
Non-final Office Action for U.S. Appl. No. 12/015,558 dated Aug. 13, 2010, 9 pages.
Non-final Office Action for U.S. Appl. No. 11/928,681 dated Feb. 2, 2012, 4 pages.
Notice of Allowance for U.S. Appl. No. 29/303,312 dated Mar. 1, 2010, 7 pages.
Notice of Allowance for U.S. Appl. No. 29/303,314 dated Feb. 5, 2010, 6 pages.
Final Office Action for U.S. Appl. No. 29/303,314 dated Dec. 28, 2009, 6 pages.
Non-Final Office Action for U.S. Appl. No. 15/359,856, dated Oct. 18, 2019, 29 pages.
Second Office Action for Chinese Patent Application No. 201710219080.3, dated Nov. 25, 2019, 18 pages.
Advisory Action for U.S. Appl. No. 12/015,593 dated Dec. 13, 2013, 3 pages.
Non-final Office Action for U.S. Appl. No. 12/015,593 dated Mar. 14, 2014, 19 pages.
Final Office Action for U.S. Appl. No. 12/015,593 dated Jul. 7, 2014, 19 pages.
Advisory Action for U.S. Appl. No. 12/015,593, dated Oct. 16, 2014, 3 pages.
Non-Final Rejection dated Jan. 4, 2013, for U.S. Appl. No. 12/015,600, 8 pages.

(56) References Cited

OTHER PUBLICATIONS

Non-final Office Action for U.S. Appl. No. 12/015,600 dated Aug. 5, 2013, 8 pages.
Final Office Action for U.S. Appl. No. 12/015,600 dated Apr. 29, 2014, 9 pages.
Advisory Action for U.S. Appl. No. 12/015,600 dated Jul. 16, 2014, 3 pages.
Non-final Office Action for U.S. Appl. No. 12/887,165 dated Apr. 10, 2013, 13 pages.
Notice of Allowance for U.S. Appl. No. 12/887,165 dated Sep. 3, 2013, 10 pages.
Final Rejection dated Dec. 27, 2012, for U.S. Appl. No. 13/183,901, 10 pages.
Advisory Action for U.S. Appl. No. 13/183,901 dated Mar. 11, 2013, 3 pages.
Non-final Office Action for U.S. Appl. No. 13/183,901 dated Oct. 4, 2013, 10 pages.
Final Office Action for U.S. Appl. No. 13/183,901 dated Feb. 3, 2014, 10 pages.
Advisory Action and Applicant-Initiated Interview Summary for U.S. Appl. No. 13/183,901 dated Apr. 21, 2014, 5 pages.
Final Office Action for U.S. Appl. No. 13/368,976 dated Mar. 11, 2013, 8 pages.
Advisory Action for U.S. Appl. No. 13/368,976 dated Jul. 10, 2013, 3 pages.
Notice of Allowance for U.S. Appl. No. 13/368,976 dated Aug. 30, 2013, 9 pages.
Final Office Action for U.S. Appl. No. 13/242,068, dated Feb. 14, 2013, 10 pages.
Non-final Office Action for U.S. Appl. No. 13/242,068 dated Jul. 3, 2013, 7 pages.
Notice of Allowance for U.S. Appl. No. 13/242,068 dated Nov. 12, 2013, 10 pages.
Final Office Action for U.S. Appl. No. 13/367,865 dated Mar. 4, 2013, 7 pages.
Notice of Allowance for U.S. Appl. No. 13/367,865 dated May 23, 2013, 9 pages.
Final Office Action for U.S. Appl. No. 13/367,908 dated Feb. 27, 2013, 7 pages.
Advisory Action for U.S. Appl. No. 13/367,908 dated May 22, 2013, 3 pages.
Notice of Allowance for U.S. Appl. No. 13/367,908 dated Aug. 19, 2013, 8 pages.
European Search Report for patent application 06801969.4 dated Nov. 5, 2012, 4 pages.
Examination Report for Indian patent application 563/MUMNP/2009 dated Oct. 31, 2012, 1 pages.
Examination Report dated Oct. 17, 2012, for European Application No. 07716444.0, 5 pages.
Examination Report dated Nov. 16, 2012, for European Application No. 06801969.4, 6 pages.
Examination Report for European Patent Application No. 07716441.6 dated May 19, 2014, 4 pages.
International Search Report dated Jan. 7, 2013, for PCT/US12/44650, 44 pages.
International Preliminary Report on Patentability for PCT/US2012/044650 dated Jan. 16, 2014, 41 pages.
Examination Report for Indian Patent Application No. 564/MUMNP/2009, dated Jan. 30, 2013, 1 page.
Examination Report for Indian Patent Application No. 555/MUMNP/2009, dated Apr. 15, 2013, 1 page.
European Search Report for European Patent Application No. 08727830.5 dated Dec. 20, 2012, 3 pages.
Examination Report for European Patent Application No. 08727830.5 dated Jan. 15, 2013, 5 pages.
Examiner's Decision of Rejection for Japanese Patent Application No. 2009-525537 dated Jan. 7, 2014, 6 pages.
First Office Action for Chinese patent application 201310017764.7 dated Mar. 31, 2014, 20 pages.

First Office Action for Chinese patent application 201310017761.3 dated May 6, 2014, 12 pages.
Second Office Action for Chinese patent application 201210077169.8 dated May 20, 2014, 3 pages (no translation).
Translation of Notice of Rejection for Japanese Patent Application No. 2009-525529 dated May 14, 2013, 5 pages.
English translation of Final Japanese Office Action for patent application 2009-544825 dated Jan. 29, 2013, 4 pages.
Examiner's Decision of Rejection for Japanese Patent Application No. 2009-544825 dated Jan. 7, 2014, 6 pages.
English translation of Final Japanese Office Action for patent application 2009-525537 dated Jan. 29, 2013, 4 pages.
First Office Action for Chinese patent application 201210077169.8 dated Nov. 26, 2013, 18 pages.
First Office Action for Chinese patent application 201210077192.7 dated Nov. 22, 2013, 12 pages.
Non-Final Office Action for U.S. Appl. No. 12/015,600 dated Oct. 31, 2014, 9 pages.
Foulks, Gary N. "The Correlation Between the Tear Film Lipid Layer and Dry Eye Disease," Survey of Ophthalmology, vol. 52, Issue 4, Jul.-Aug. 2007, Elsevier Inc., pp. 369-374.
Notice of Allowance for U.S. Appl. No. 29/303,317 dated Feb. 1, 2010, 8 pages.
Non-final Office Action for U.S. Appl. No. 29/303,317 dated Sep. 1, 2009, 10 pages.
Notice of Allowance for U.S. Appl. No. 12/015,567 dated May 20, 2011, 8 pages.
Non-final Office Action for U.S. Appl. No. 12/015,567 dated Aug. 16, 2010, 9 pages.
Non-final Office Action for U.S. Appl. No. 12/015,576 dated Jul. 19, 2010, 11 pages.
Notice of Allowance for U.S. Appl. No. 12/015,584 dated Jul. 8, 2011, 4 pages.
Notice of Allowance for U.S. Appl. No. 12/015,584 dated Jun. 29, 2011, 7 pages.
Final Office Action for U.S. Appl. No. 12/015,584 dated May 27, 2011, 7 pages.
Non-final Office Action for U.S. Appl. No. 12/015,584 dated Aug. 23, 2010, 9 pages.
Non-final Office Action for U.S. Appl. No. 12/015,600 dated Mar. 19, 2012, 6 pages.
Notice of Allowance for U.S. Appl. No. 12/015,675 dated Oct. 26, 2011, 9 pages.
Non-final Office Action for U.S. Appl. No. 12/015,675 dated May 10, 2011, 7 pages.
Notice of Allowance for U.S. Appl. No. 12/015,683 dated Oct. 26, 2011, 8 pages.
Non-final Office Action for U.S. Appl. No. 12/015,683 dated May 6, 2011, 14 pages.
Notice of Allowance for U.S. Appl. No. 12/015,721 dated Nov. 30, 2011, 8 pages.
Advisory Action for U.S. Appl. No. 12/015,721 dated Aug. 31, 2011, 3 pages.
Final Office Action for U.S. Appl. No. 12/015,721 dated Jun. 8, 2011, 12 pages.
Non-final Office Action for U.S. Appl. No. 12/015,721 dated Jan. 5, 2011, 12 pages.
Notice of Allowance for U.S. Appl. No. 29/344,914 dated Mar. 7, 2011, 8 pages.
Notice of Allowance for U.S. Appl. No. 29/344,914 dated Jan. 12, 2011, 7 pages.
English translation of Japanese Office Action for patent application 2009-525536 dated Jan. 10, 2012, 6 pages.
International Search Report for PCT/US07/00493 dated Oct. 1, 2007, 1 page.
English translation of First Office Action for Chinese patent application 200780039253.8 dated Jul. 12, 2010, 6 pages.
Extended European Search Report for PCT/US2007/000525 dated Sep. 20, 2010, 9 pages.
English translation of Japanese Office Action for patent application 2009-544825 dated Jan. 10, 2012, 9 pages.
International Search Report for PCT/US07/00525 dated Dec. 3, 2007, 12 pages.

(56) References Cited

OTHER PUBLICATIONS

Extended European Search Report for patent application 07716445.7-1269 dated Apr. 7, 2011, 9 pages.
English translation of Japanese Office Action for patent application 2009-525537 dated Jan. 10, 2012, 4 pages.
International Search Report for PCT/US07/00508 dated Nov. 2, 2007, 1 page.
Second Chinese Office Action for patent application 200880008741.7 dated Mar. 29, 2012, 7 pages.
English translation of First Chinese Office Action for patent application 200880008741.7 dated Jul. 20, 2011, 7 pages.
Office Action for Israeli patent application 199920 dated May 22, 2011, 2 pages.
International Search Report for PCT/US08/51309 dated May 20, 2008, 24 pages.
English translation of First Office Action for Chinese patent application 200680056181.3 dated Jun. 12, 2010, 6 pages.
International Search Report for PCT/US06/32544 dated May 12, 2008, 8 pages.
Notice of Allowance for U.S. Appl. No. 12/015,576 dated May 20, 2011, 8 pages.
Final Office Action for U.S. Appl. No. 11/434,033 dated Mar. 15, 2012, 9 pages.
Finis, D. et al., "Meibom-Drusen-Dysfunktion," Klinische Monatsblatter fur Augenheilkunde, vol. 229, No. 5, Mar. 2012, pp. 506-513 (Abstract translated only).
Non-final Office Action for U.S. Appl. No. 13/183,901 dated Jun. 4, 2012, 46 pages.
Korb, et al., "Forceful Meibomian Gland Expression with a Standardized Force of 8 PSI in Patients with Obstructive Meibomian Gland Dysfunction," ARVO Annual Meeting, Poster Session, Program No. 3819, Poster Board No. D952, May 3, 2011, 2 pages (Abstract Only).
Korb, et al., "Prevalence of lid wiper epitheliopathy in subjects with dry eye signs and symptoms," Cornea, vol. 29, No. 4, Apr. 2012, pp. 377-383.
Yoshitomi, et al., "Meibomian Gland Compressor and Cataract Surgery," New Ophthalmology, Japan, 2001, vol. 18, No. 3, pp. 321-323.
Willis, et al., "Meibomian gland function, lid wiper epitheliopathy, and dry eye symptoms," ARVO Annual Meeting, May 2011, pp. 3740 (Abstract only).
Second Office Action for Japanese patent application 2009-525529 dated Jun. 5, 2012, 8 pages.
Extended European Search Report for patent application 07716441.6 dated Sep. 4, 2012, 7 pages.
Foulks, G. et al., "Comparative Effectiveness of Azithromycin and Doxycycline in Therapy of Meibomian Gland Dysfunction," ARVO Annual Meeting, May 2011, pp. 3816 (Abstract only).
Korb, et al., "Restoration of meibomian gland function post Lipiflow treatment," ARVO Annual Meeting, May 2011, pp. 3818 (Abstract only).
Maskin, S. et al., "Intraductal Meibomian Gland Probing with Adjunctive Intraductal Microtube Steriod Injection (MGPs) for Meibomian Gland Dysfunction," ARVO Annual Meeting, May 2011, pp. 3817 (Abstract only).
McCann, L. et al., "Effect of First Line Management Therapies on Dry Eye Disease," ARVO Annual Meeting, May 2011, pp. 3829 (Abstract only).
Second Office Action for Chinese Patent Application No. 201210127347.3, dated Nov. 2, 2014, 7 pages.
Second Office Action for Chinese Patent Application No. 201310017764.7, dated Nov. 15, 2014, 12 pages.
Baumann, A. et al., "Meibomian gland dysfunction: A comparative study of modern treatments," French Journal of Ophthalmology, vol. 37, No. 4, Apr. 2014, Elsevier Masson SAS, pp. 303-312.
Bron, Anthony J. et al., "Rethinking Dry Eye Disease: A Perspective on Clinical Implications," The Ocular Surface, vol. 12, No. 2S, Apr. 2014, Elsevier Inc., 31 pages.

Zhang, J. et al., "A Meibomian Gland Massage Mechanism for Upper and Lower Eyelids Based on Anti-phase Rolling and Enveloping Movement," Chinese Journal of Medical Instrumentation, vol. 38, No. 4, Jul. 2014, pp. 255-258, 273.
Notice of Allowance for U.S. Appl. No. 11/931,398, dated Jan. 16, 2015, 8 pages.
Non-Final Office Action for U.S. Appl. No. 11/931,914, dated Jun. 8, 2015, 25 pages.
Non-Final Office Action for U.S. Appl. No. 12/015,593, dated Jun. 4, 2015, 20 pages.
Final Office Action for U.S. Appl. No. 12/015,600 dated May 21, 2015, 12 pages.
Notice of Allowance for U.S. Appl. No. 13/183,901, dated Aug. 12, 2015, 11 pages.
Examination Report for European Patent Application No. 06801969.4, dated Jul. 6, 2015, 5 pages.
Third Office Action for Chinese Patent Application No. 201210127347.3, dated Jun. 26, 2015, 7 pages.
Notice of Rejection for Japanese Patent Application No. 2013-226709, dated Mar. 24, 2015, 10 pages.
Aragona, Pasquale et al., "Towards a dynamic customised therapy for ocular surface dysfunctions," British Journal of Ophthalmology, vol. 97, No. 8, Aug. 2013, pp. 955-960.
Author Unknown, "Appendages of the eye," The Free Dictionary by Farlex, Medical Dictionary, retrieved on Feb. 8, 2016, medical-dictionary.thefreedictionary.com/appendages+of+the+eye, Farlex and Partners, 1 page.
Author Unknown, "Simple Definition of AROUND" Merriam-Webster's Learner's Dictionary, accessed Aug. 15, 2016, www.merriam-webster.com/dictionary/around, 1 page.
Author Unknown, Definition of "Orbit," Miller-Keane Encyclopedia and Dictionary of Medicine, Nursing, and Allied Health, Seventh Edition, 2003, Saunders, medical-dictionary.thefreedictionary.com/orbit, accessed Sep. 29, 2016, 1 page.
Author Unknown, "Medical Definition of ORBIT," Merriam-Webster Dictionary, retrieved Feb. 8, 2016, www.merriam-webster.com/medical/orbit, Merriam-Webster, Incorporated, 2 pages.
Author Unknown, "Medical Definition of PERIORBITAL," Merriam-Webster: Medical Dictionary, accessed Aug. 15, 2016, www.merriam-webster.com/medical/periorbital, 1 page.
Author Unknown, "Home," http://www.heatedeyepad.com/home.html, accessed Dec. 16, 2016, Digital Heat, 2 pages.
Author Unknown, "Product," http://www.heatedeyepad.com/product.html, accessed Dec. 16, 2016, Digital Heat, 2 pages.
Blackie, Caroline A., et al., "Treatment for meibomian gland dysfunction and dry eye symptoms with a single-dose vectored thermal pulsation: a review," Current Opinion In Ophthamology, vol. 26, Issue 4, Jul. 2015, Lippincott Williams & Wilkins, pp. 306-313.
Di Pascuale, Mario A., et al, "Lipid tear deficiency in persistent dry eye after laser in situ keratomileusis and treatment results of new eye-warming device," Journal of Cataract & Refractive Surgery, vol. 31, Issue 9, Sep. 2005, Elsevier, pp. 1741-1749.
Doan, S., et al., "Evaluation of an eyelid warming device (Blephasteam®) for the management of ocular surface diseases in France: The ESPOIR study," Journal Francais d'Ophtalmologie, vol. 37, Issue 10, Oct. 1, 2014, Elsevier Masson SAS, pp. 763-772.
Goslin, Krysta, et al., "Evaluation of a Single Thermal Pulsation Treatment for Dry Eye and Meibomian Gland Dysfunction and Likelihood of Positive SJO Test," Investigative Ophthalmology & Visual Science, vol. 56, Jun. 2015, The Association for Research in Vision and Ophthalmology, 2 pages (Meeting Abstract).
Hynes, Michael, et al., "Design of a subtarsal ultrasonic transducer for mild hyperthermia of meibomian glands treating Dry Eye Disease," Investigative Ophthalmology & Visual Science, vol. 56, Jun. 2015, The Association for Research in Vision and Ophthalmology, 3 pages (Meeting Abstract).
Hynes, Michael, B., et al., "Design of a Subtarsal Ultrasonic Transducer for Mild Hyperthermia Treatment of Dry Eye Disease," Ultrasound in Medicine & Biology, vol. 42, Issue 1, Jan. 2016, Elsevier Inc., pp. 232-242.
Dudee, Jitander S., "Affidavit," mailed Aug. 26, 2016, 2 pages.

(56) References Cited

OTHER PUBLICATIONS

Matsumoto, Yukihiro, et al., "Efficacy of a New Warm Moist Air Device on Tear Functions of Patients With Simple Meibomian Gland Dysfunction," Cornea, vol. 25, Issue 6, Jul. 2006, Lippincott Williams & Wilkins, pp. 644-650.
Nakayama, Naohiko, et al., "Analysis of Meibum Before and After Intraductal Meibomian Gland Probing in Eyes with Obstructive Meibomian Gland Dysfunction," Cornea, vol. 34, Issue 10, Oct. 2015, Wolters Kluwer Health, Inc., pp. 1206-1208.
Nakayama, Naohiko, et al., "Analysis of Meibum Before and Following Intraductal Meibomian Gland Probing for Eyes with Obstructive Meibomian Gland Dysfunction," Investigative Ophthalmology & Visual Science, vol. 56, Jun. 2015, The Association for Research in Vision and Ophthalmology, 2 pages (Meeting Abstract).
Ngo, William, et al., "Effect of Lid Debridement-Scaling on Dry Eye Signs and Symptoms in Sjogren's Syndrome," Investigative Ophthalmology & Visual Science, vol. 56, Jun. 2015, The Association for Research in Vision and Ophthalmology, 2 pages (Meeting Abstract).
Tanabe, Hirotaka, et al., "Effect of Eye Shampoo for Obstructive Meibomian Gland Disease," Investigative Ophthalmology & Visual Science, vol. 56, Jun. 2015, The Association for Research in Vision and Ophthalmology, 2 pages (Meeting Abstract).
Thode, Adam R., et al., "Current and Emerging Therapeutic Strategies for the Treatment of Meibomian Gland Dysfunction (MGD)," Drugs, vol. 75, Issue 11, Jul. 1, 2015, Springer International Publishing, pp. 1177-1185.
Vegunta, Srav, et al., "Tear osmolarity measurements in ocular graft-versus-host disease patients undergoing intense pulsed light (IPL) and meibomian gland expression (MGX)," Investigative Ophthalmology & Visual Science, vol. 56, Jun. 2015, The Association for Research in Vision and Ophthalmology, 2 pages (Meeting Abstract).
Vora, Gargi K., et al., "Intense pulsed light therapy for the treatment of evaporative dry eye disease," Current Opinion in Ophthalmology, vol. 26, Issue 4, Jul. 2015, Wolters Kluwer Health, Inc., pp. 314-318.
Non-Final Office Action for U.S. Appl. 11/541,308, dated Sep. 29, 2016, 26 pages.
Non-Final Office Action for U.S. Appl. No. 14/618,392, dated Sep. 30, 2016, 11 pages.
Non-Final Office Action for U.S. Appl. No. 14/074,123, dated Dec. 29, 2016, 23 pages.
Final Office Action for U.S. Appl. No. 12/015,593, dated Feb. 16, 2016, 22 pages.
Non-Final Office Action for U.S. Appl. No. 14/510,843, dated Feb. 4, 2016, 10 pages.
Final Office Action for U.S. Appl. No. 14/510,843, dated Aug. 25, 2016, 13 pages.
Advisory Action for U.S. Appl. No. 12/015,600 dated Nov. 3, 2015, 3 pages.
Notice of Allowance for U.S. Appl. No. 12/015,600, dated Jan. 20, 2016, 7 pages.
Non-Final Office Action for U.S. Appl. No. 13/590,828, dated Feb. 26, 2016, 11 pages.
Final Office Action for U.S. Appl. No. 13/590,828, dated Sep. 9, 2016, 12 pages.
Non-Final Office Action for U.S. Appl. No. 14/746,328, dated May 31, 2017, 11 pages.
Non-Final Office Action for U.S. Appl. No. 11/541,308, dated Apr. 27, 2017, 21 pages.
Non-Final Office Action for U.S. Appl. No. 14/618,392, dated Jun. 28, 2017, 23 pages.
Final Office Action for U.S. Appl. No. 14/074,123, dated Jun. 8, 2017, 26 pages.
Advisory Action for U.S. Appl. No. 13/590,828, dated Jan. 27, 2017, 3 pages.
No Author, "arGentis Licenses Third Treatment for Dry Eye Syndrome", Business Wire, May 12, 2008, accessed Jun. 4, 2008, 2 pages.
No Author, "New Over-the-Counter Dry Eye Drop Now Available to Help Estimated 40 Percent of Americans Who Suffer from Occasional or Chronic Dry Eye", Business Wire News Release, Mar. 31, 2008, accessed Jun. 5, 2008, 4 pages.
Akyol-Salman, Ilknur et al., "Efficacy of Topical N-Acetylcysteine in the Treatment of Meibomian Gland Dysfunction," Journal of Ocular Pharmacology and Therapeutics, vol. 26, No. 4, Aug. 1, 2010, pp. 329-333.
Aronowicz, JD et al. "Short Term Oral Minocycline Treatment of Meibomiantis," Br. J. Ophthalmol, vol. 90, No. 7, Jul. 2006, pp. 856-860.
Blackie, Caroline A. et al., "Inner Eyelid Surface Temperature as a Function of Warm Compress Methodology," Optometry and Vision Science, vol. 85, No. 8, Aug. 2008, pp. 675-683.
Blackie, Caroline A. et al., "Nonobvious Obstructive Meibomian Gland Dysfunction," Cornea, vol. 29, No. 12, Dec. 2010, pp. 1333-1345.
Blackie, Caroline A. et al., "Recovery Time of an Optimally Secreting Meibomian Gland," Cornea, vol. 28, No. 3, Apr. 2009, pp. 293-297.
Butovich, Igor et al., "Meibomian Lipid Films and the Impact of Temperature," Investigative Opthalmology & Visual Science, vol. 51, No. 11, Jul. 2010, pp. 5508-5518.
Cunniffe, M. Geraldine et al., "Topical Antiglaucoma Treatment with Prostaglandin Analogues May Precipitate Meibomian Gland Disease," Ophthalmic Plastic and Reconstructive Surgery, Sep.-Oct. 2011, vol. 27, No. 5, Lippincott Williams and Wilkins, Philadelphia, PA, p. 128-129.
Dausch, Eva et al., "Dry Eye Syndrome in Women's Health and Gynecology: Etiology, Pathogenesis and Current Therapeutic Strategies," Geburtshilfe und Frauenheilkunde, vol. 70, No. 9, Jan. 1, 2010, pp. 707-711. (Abstract Only).
Donnenfeld, Eric et al., "Topical Ophthalmic Cyclosporine: Pharmacology and Clinical Uses," Survey of Ophthalmology, vol. 54, No. 3, May/Jun. 2009, pp. 321-338.
Foulks, Gary N. et al., "Topical Azithromycin Therapy for Meibomian Gland Dysfunction: Clinical Response and Lipid Alterations," Cornea, vol. 29, No. 7, Jul. 2010, pp. 781-788.
Foulks, Gary N. et al., "Meibomian Gland Dysfunction: The Past, Present, and Future," Eye and Contact Lens, vol. 36, No. 5, Sep. 2010, pp. 249-253.
Friedland, B., et al., "A Novel Thermodynamic Treatment for Meibomian Gland Dysfunction," Current Eye Research, vol. 36, No. 2, Feb. 2011, pp. 79-87.
Geerling, G., et al., "The international workshop on meibomian gland dysfunction: report of the subcommittee on management and treatment of meibomian gland dysfunction," Mar. 2011, Investigative Ophthalmology & Visual Science, vol. 52, No. 4., pp. 2050-2064.
Goto, E., et al. "Treatment of Non-Inflamed Obstructive Meibomian Gland Dysfunction by an Infrared Warm Compression Device," Br J. Ophthalmology, vol. 86, Dec. 2002, pp. 1403-1407.
Goto, Eiki, et al., "Tear Evaporation Dynamics in Normal Subjects and Subjects with Obstructive Meibomian Gland Dysfunction," Investigative Ophthalmology & Visual Science, vol. 44, No. 2, Feb. 2003, pp. 533-539.
Greiner, J., "A Single LipiFlow Thermal Pulsation System Treatment Improves Meibomian Gland Function and Reduces Dry Eye Symptoms for 9 months," Current Eye Research, vol. 37 No. 4, Apr. 2012, pp. 272-278.
Gupta, S. et al. "Docetaxel-Induced Meibomian Duct Inflammation and Blockage Leading to Chalazion Formation," Prostate Cancer and Prostatic Diseases, vol. 10, No. 4, Apr. 2007, pp. 396-397.
Haque, Reza M. et al., "Multicenter Open-label Study Evaluating the Efficacy of Azithromycin Opthalmic Solution 1% on the Signs and Symptoms of Subjects with Blepharitis," Cornea, vol. 29, No. 8, Aug. 2010, pp. 871-877.

(56) References Cited

OTHER PUBLICATIONS

Holifield, Karintha and Lazzaro, Douglas R., "Case report: Spontaneous stenotrophomonas maltophilia keratitis in a diabetic patient," Eye and Contact Lens, Sep. 2011, vol. 37, No. 5, Philadelphia PA, pp. 326-327.
Knop, E. et al., "Meibomian Glands: Part III—Dysfunction—Argument for a Discrete Disease Entity and as an Important Cause of Dry Eye," Ophthalmologe, vol. 106, No. 11, Nov. 2009, pp. 966-979. (Abstract Only).
Knop, E. et al., "Meibomian Glands: Part IV—Functional Interactions in the Pathogenesis of Meibomian Gland Dysfunction (MGD)," Ophthalmologe, vol. 106, No. 11, Nov. 2009, pp. 980-987. (Abstract Only).
Kokke, K.H. et al., "Oral Omega-6 Essential Fatty Acid Treatment in Contact Lens Associated Dry Eye," Contact Lens and Anterior Eye, vol. 31, No. 3, Jun. 2008, pp. 141-146.
Korb, Donald et al., "The Effect of Two Novel Lubricant Eye Drops on Tear Film Lipid Layer Thickness in Subjects with Dry Eye Symptoms," Optom. Vis. Sci., vol. 82, No. 7, 2005, pp. 594-601.
Korb, Donald R. and Blackie, Caroline A., "Meibomian gland therapeutic expression: Quantifying the applied pressure and the limitation of resulting pain," Eye and Contact Lens, Sep. 2011, vol. 37, No. 5, Philadelphia, PA, pp. 298-301.
Korb, Donald R. et al., "Increase in Tear Film Lipid Layer Thickness Following Treatment of Meibomian Gland Dysfunction", Lacrimal Gland, Tear Film & Dry Eye Syndromes, vol. 350, Plenum Press, 1994, pp. 293-298.
Korb, Donald R. et al., "Lid Wiper Epitheliopathy and Dry Eye Symptoms," Eye & Contact Lens, vol. 31, No. 1, Jan. 2005, pp. 2-8.
Korb, Donald R. et al., "Restoration of Meibomian Gland Functionality with Novel Thermodynamic Treatment Device—A Case Report," Cornea, vol. 29, No. 8, Aug. 2010, pp. 930-933.
Korb, Donald R. et al., "Tear Film Lipid Layer Thickness as a Function of Blinking," Cornea, vol. 13, No. 4, Jul. 1994, pp. 354-359.
Korb, Donald R. et al., Slide entitled "Inner Eyelid Surface Temperature as a Function of Warm Compress Methodology," from presentation entitled "The Greatest Anterior Segment Disease and Contact Lens Complications Course," AOA Meeting, Seattle, Washington, Jun. 27, 2008, 2 pages.
Korb, Donald R., O.D., et al., "Meibomian Gland Dysfunction and Contact Lens Intolerance," Journal of the American Optometric Association, vol. 51, No. 3, Mar. 1980, pp. 243-251.
Korb, Donald R., Slide entitled "Inner Eyelid Surface Temperature as a Function of Warm Compress Methodology," from presentation entitled "The Tear Film and Dry Eye States a Fertile Research Area," University of California at Berkeley, School of Optometry, Apr. 11, 2008. 2 pages.
Kuscu, Naci Kemal, et al., "Tear Function Changes of Postmenopausal Women in Response to Hormone Replacement Therapy," Maturitas, vol. 44, Jan. 2003pp. 63-68.
Lane, S. et al., "A New System, the LipiFlow, for the Treatment of Meibomian Gland Dysfunction," Cornea, vol. 31, No. 4, Apr. 2012, pp. 396-404.
Lemp, Michael A. et al., "Blepharitis in the United States 2009: A Survey-Based Perspective on Prevalence and Treatment." Ocululur Surface, vol. 7, No. 2 Supplement, Apr. 2009, 36 pages.
Lemp, Michael A., et al., "The Therapeutic Role of Lipids—Managing Ocular Surface Disease," Supplement to Refractive Eyecare of Ophthalmologists, vol. 9, No. 6, Jun. 2005, 14 pages.
Maskin, Steven L., "Intraductal Meibomian Gland Probing Relieves Symptoms of Obstructive Meibomian Gland Dysfunction," Cornea, vol. 29, No. 10, Oct. 2010, pp. 1145-1152.
Matsumoto, Yukihiro et al., "The Evaluation of the Treatment Response in Obstructive Meibomian Gland Disease by In Vivo Laser Confocal Microscopy," Graefes Arch Clin Exp Ophthalmol, vol. 247, No. 6, Jun. 2009, pp. 821-829.
Unknown, "Introducing: Thermofoil Heaters", Minco Bulletin HS-202, 2002, 9 pages.
Mitra, M. et al., "Tear Film Lipid Layer Thickness and Ocular Comfort after Meibomian Therapy via Latent Heat with a Novel Device in Normal Subjects," Eye, Jun. 2005, pp. 657-660.
Mori, A., et al., "Efficacy of the Treatment by the Disposable Eyelid Warming Instrument for Meibomian Gland Dysfunction," Poster Presentation, Hall A, The Association for Research and Vision in Ophthalmology Annual Meeting, Fort Lauderdale, Florida, Apr. 30, 2000, 1 page.
Mori, Asako, et al., "Disposable Eyelid-Warming Device for the Treatment of Meibomian Gland Dysfunction", Japan Journal of Ophthalmology, vol. 47, pp. 578-586, 2003.
Olson, Mary Catherine, B.A., et al., "Increase in Tear Film Lipid Layer Thickness Following Treatment with Warm Compresses in Patients with Meibomian Gland Dysfunction," Eye & Contact Lens, vol. 29, No. 2, Apr. 2003, pp. 96-99.
Paugh, J.R. et al., "Meibomian Therapy in Problematic Contact Lens Wear," Entrez PubMed, Optom Vis Sci, vol. 67, No. 11, Nov. 1990, pp. 803-806 (abstract only).
Paugh, Jerry R. et al., "Precorneal Residence Time of Artificial Tears Measured in Dry Eye Subjects," Optometry and Vision Science, vol. 85, No. 8, Aug. 2008, pp. 725-731.
Romero, Juan M., et al., "Conservative Treatment of Meibomian Gland Dysfunction," Contact Lens Association of Ophthalmology, Eye & Contact Lens, vol. 30, No. 1, Jan. 2004, pp. 14-19.
Sullivan, Benjamin D., et al., "Impact of Antiandrogen Treatment on the Fatty Acid Profile of Neutral Lipids in Human Meibomian Gland Secretions," Journal of Clinical Endocrinology & Metabolism, vol. 85, No. 12, Dec. 2000, pp. 4866-4873.
Sullivan, David et al., "Do Sex Steroids Exert Sex-Specific and/or Opposite Effects on Gene Expression in Lacrimal and Meibomian Glands?" Molecular Vision, vol. 15, No. 166, Aug. 10, 2009, pp. 1553-1572.
Suzuki, Tomo et al., "Estrogen and Progesterone Control of Gene Expression in the Mouse Meibomian Gland," Invest. Ophthalmol. Vis. Sci., vol. 49, No. 5, May 2008, pp. 1797-1818.
Intention to Grant for European Patent Application No. 16170742.7, dated Jul. 24, 2020, 43 pages.
Non-Final Office Action for U.S. Appl. No. 16/375,196, dated Jul. 21, 2020, 8 pages.
Non-Final Office Action for U.S. Appl. No. 15/359,856, dated Jun. 1, 2020, 9 pages.
Notice of Allowance for U.S. Appl. No. 16/375,196, dated Oct. 8, 2020, 7 pages.
Notice of Allowance for U.S. Appl. No. 15/359,856, dated Nov. 12, 2020, 9 pages.

\* cited by examiner

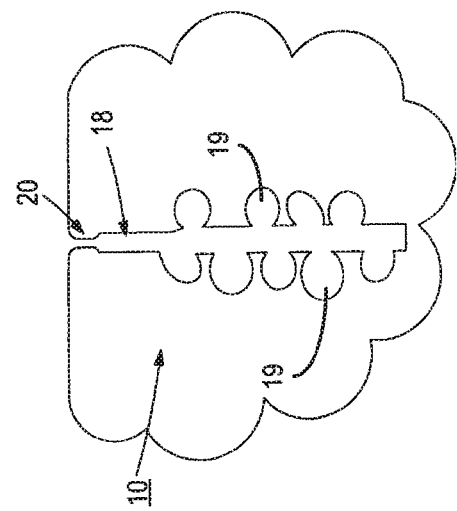
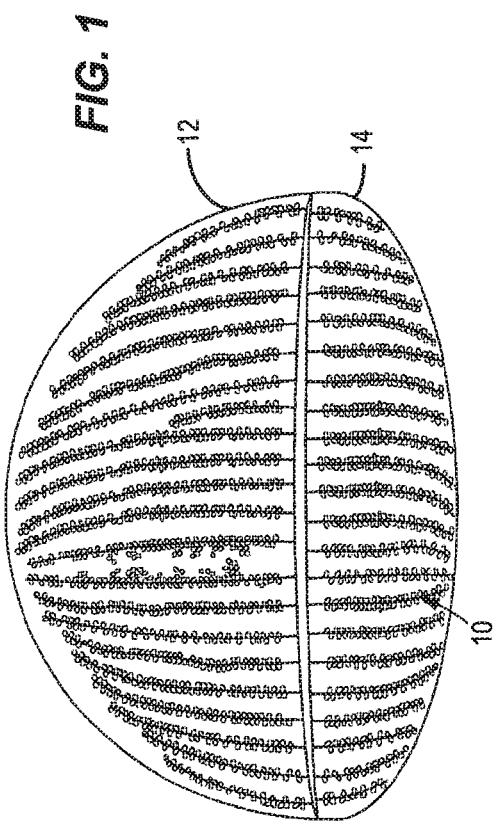
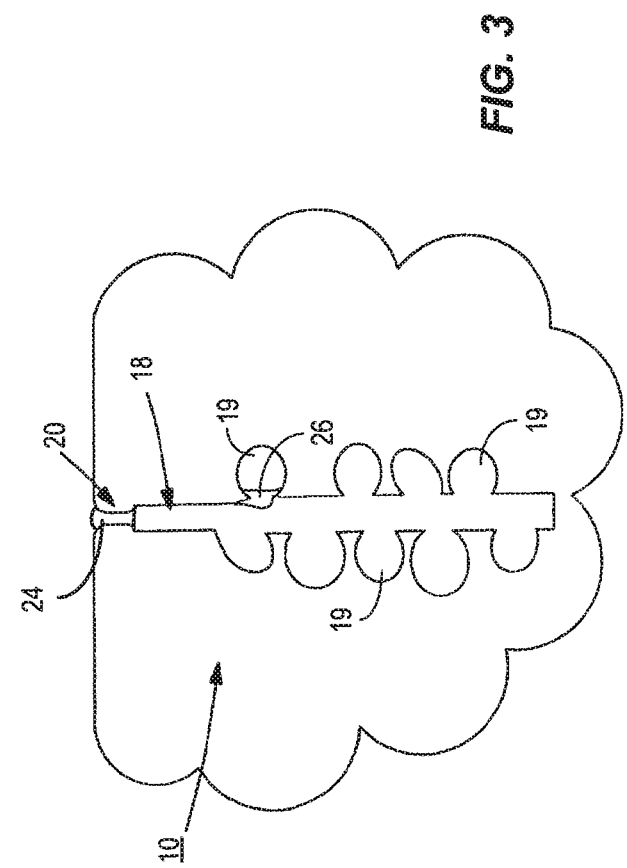

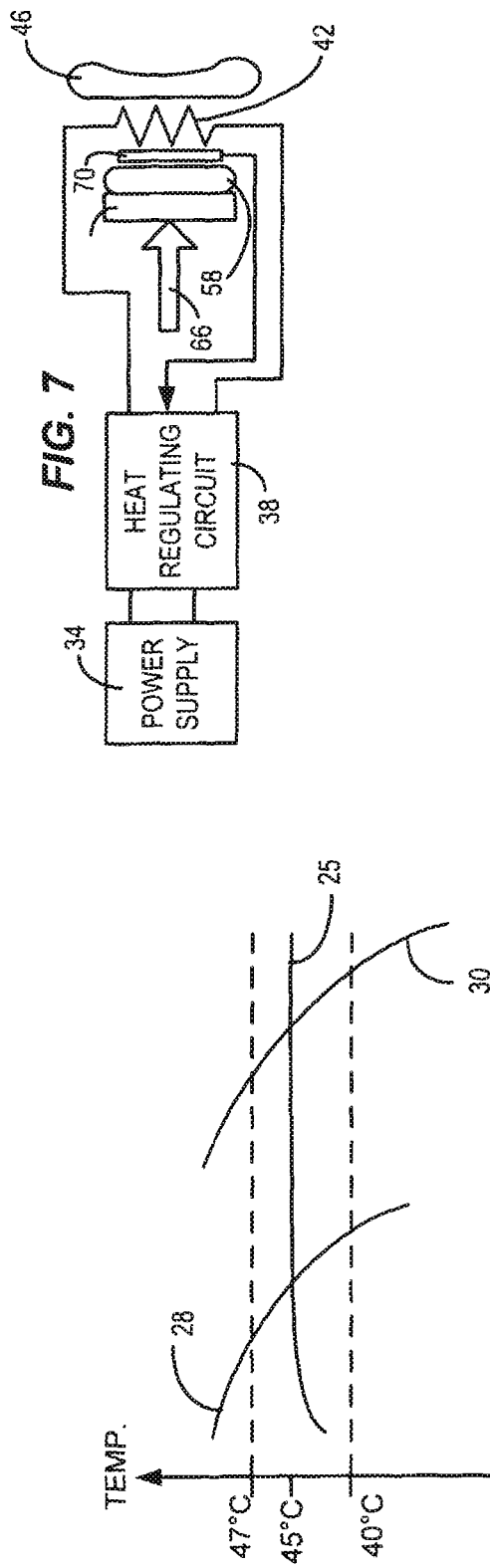
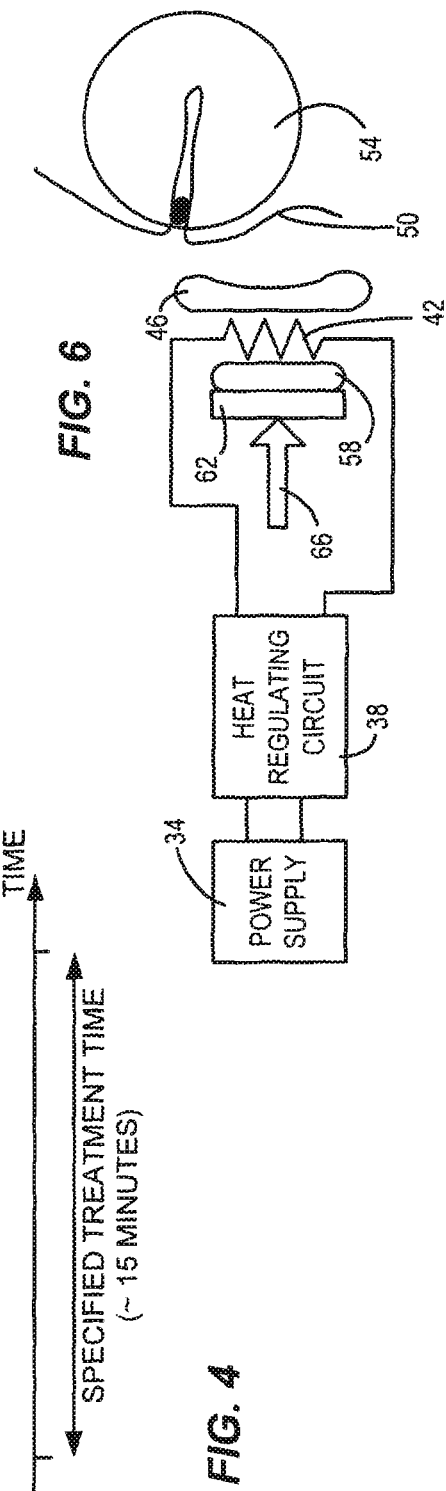

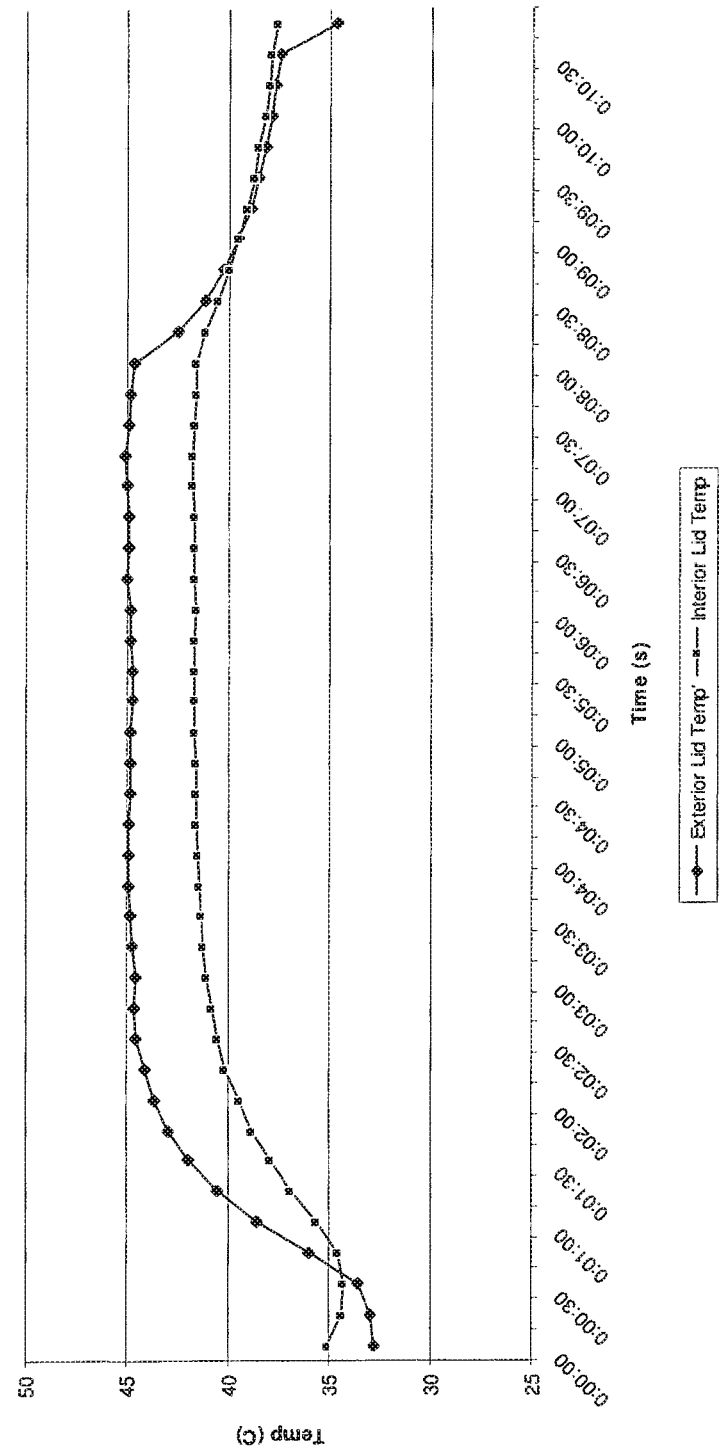

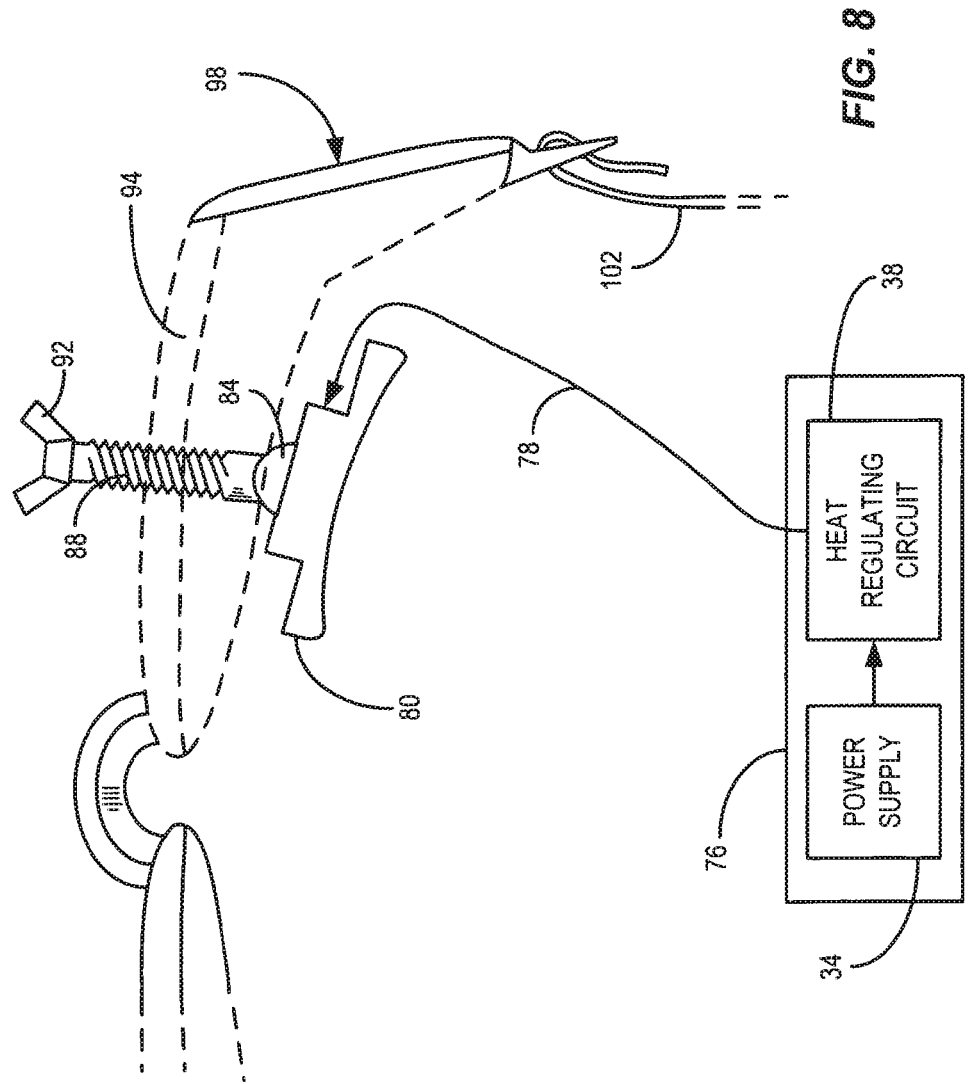

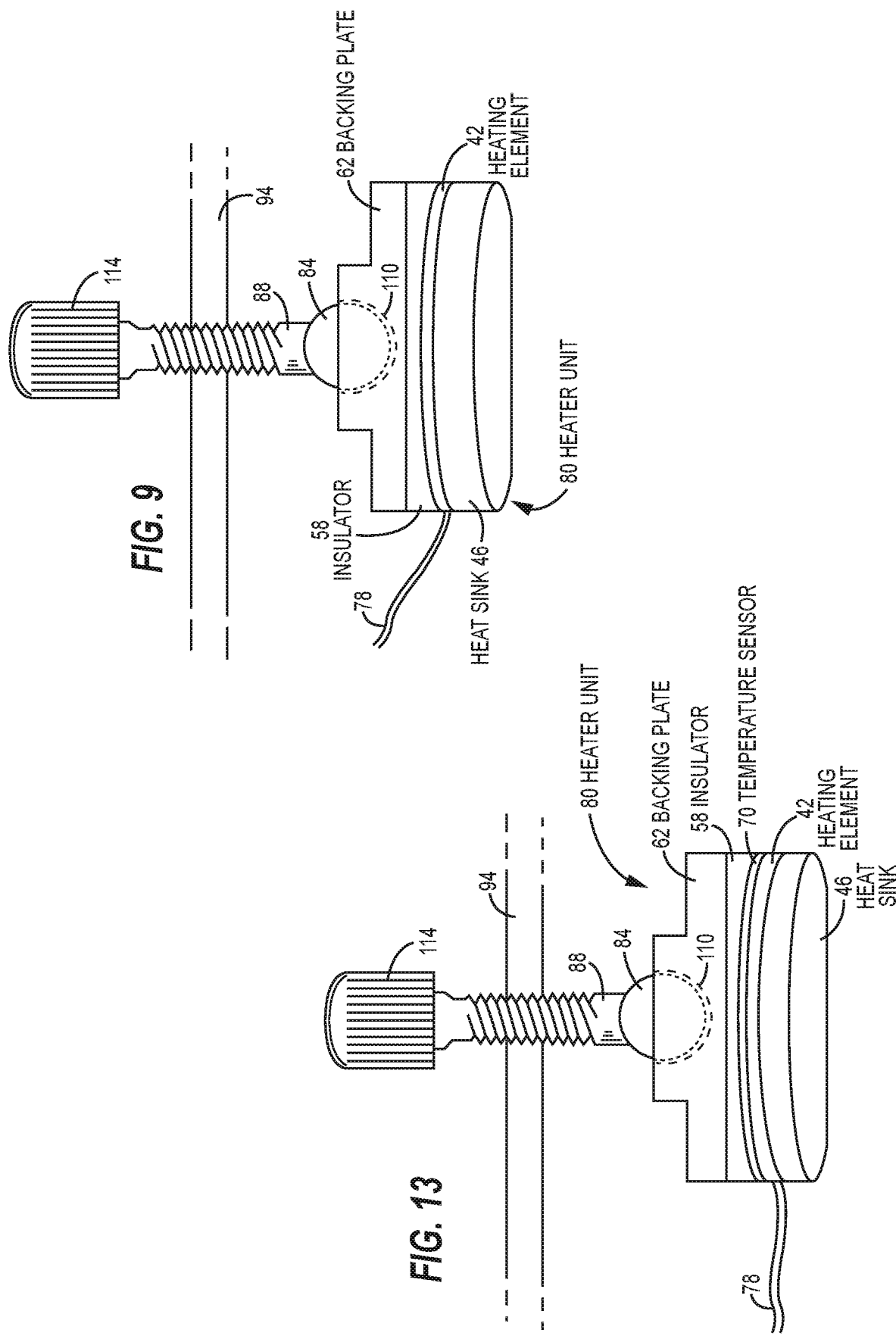

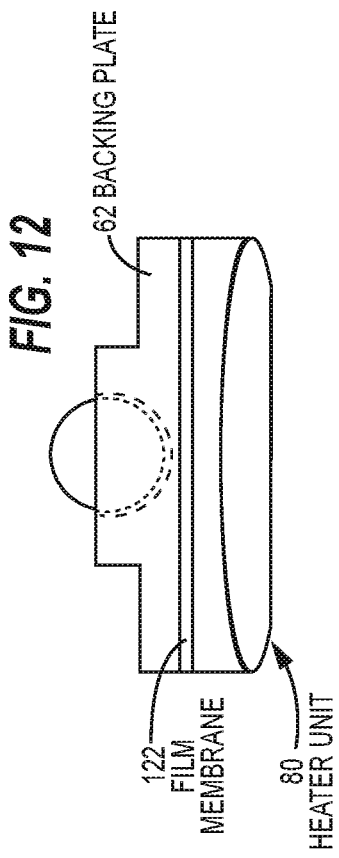
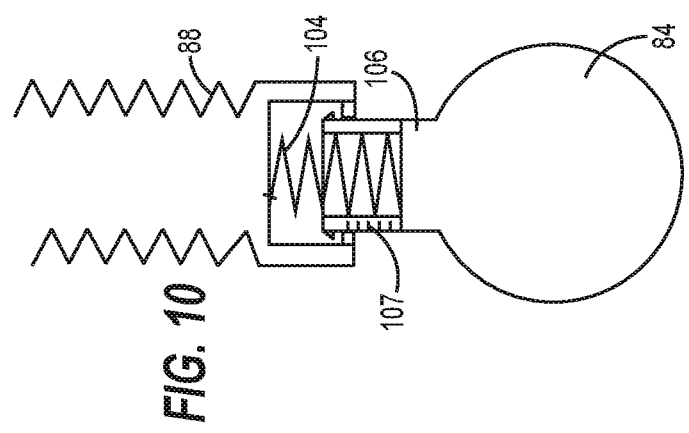

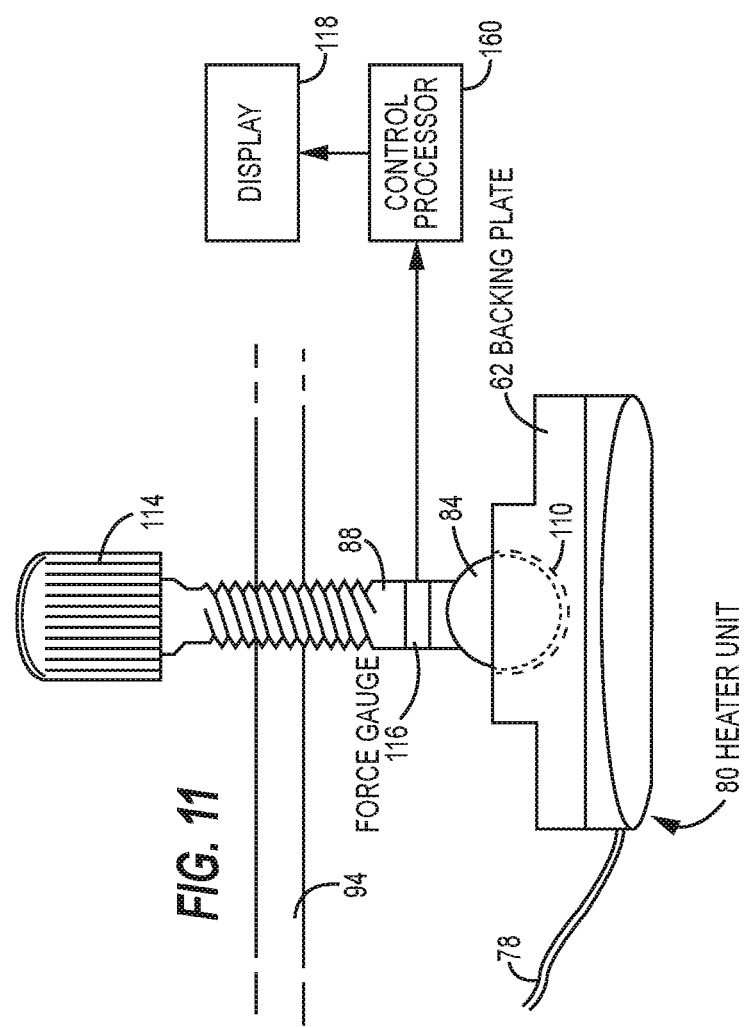

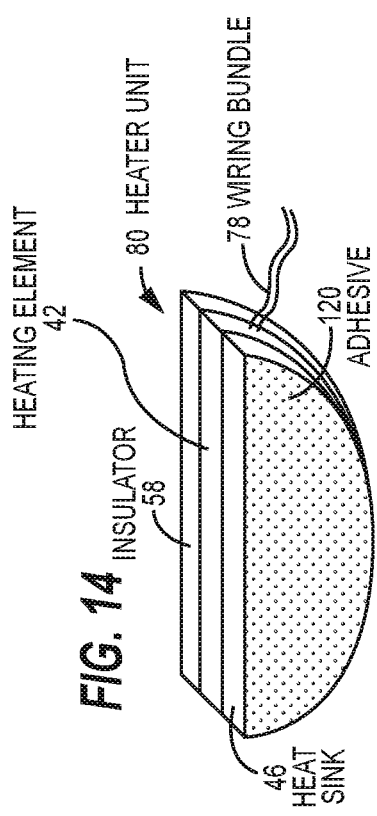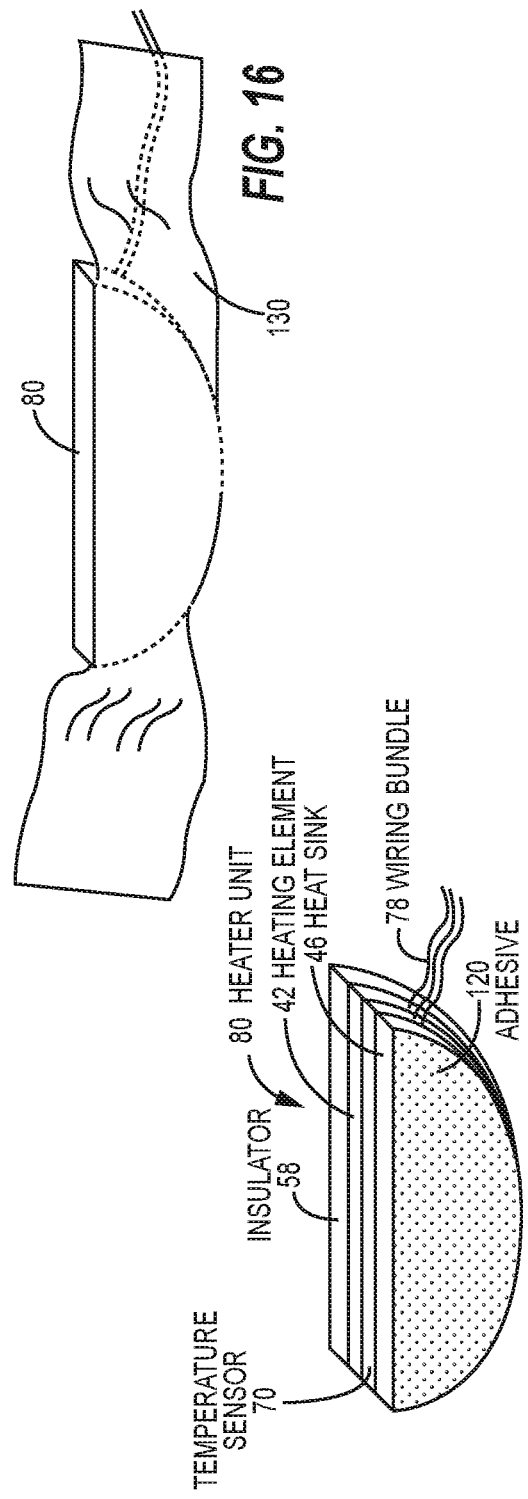

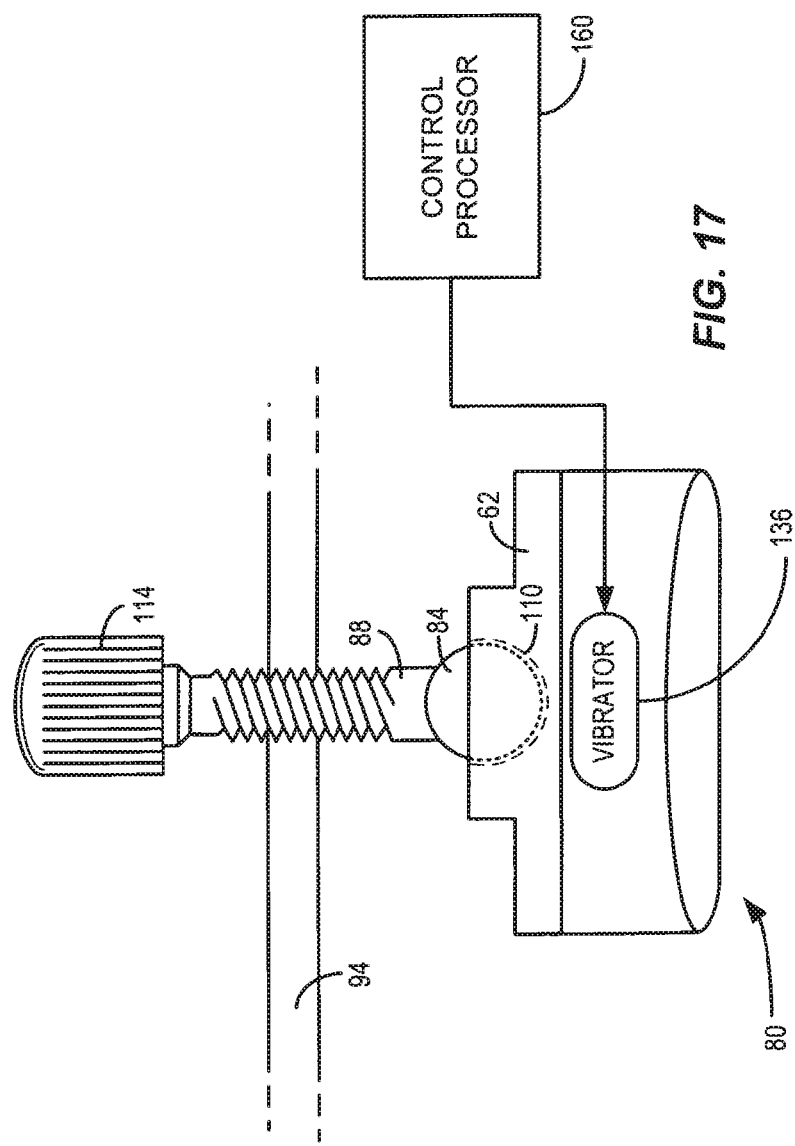

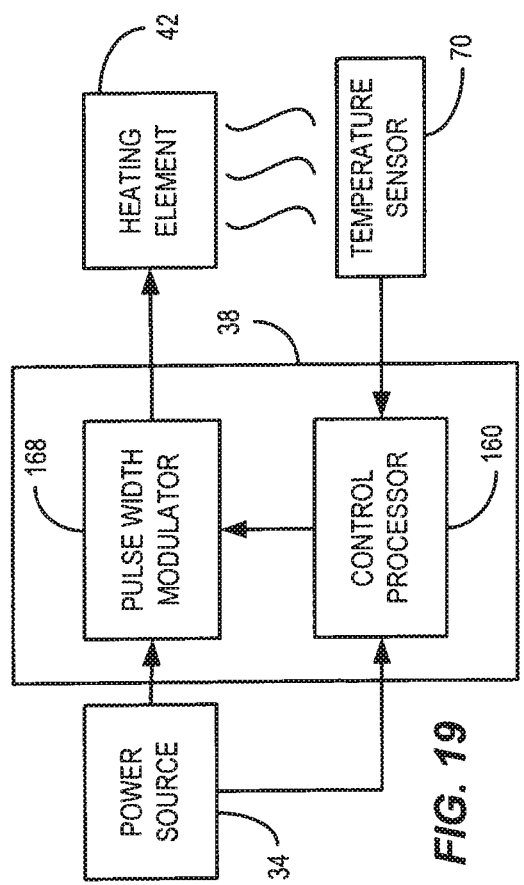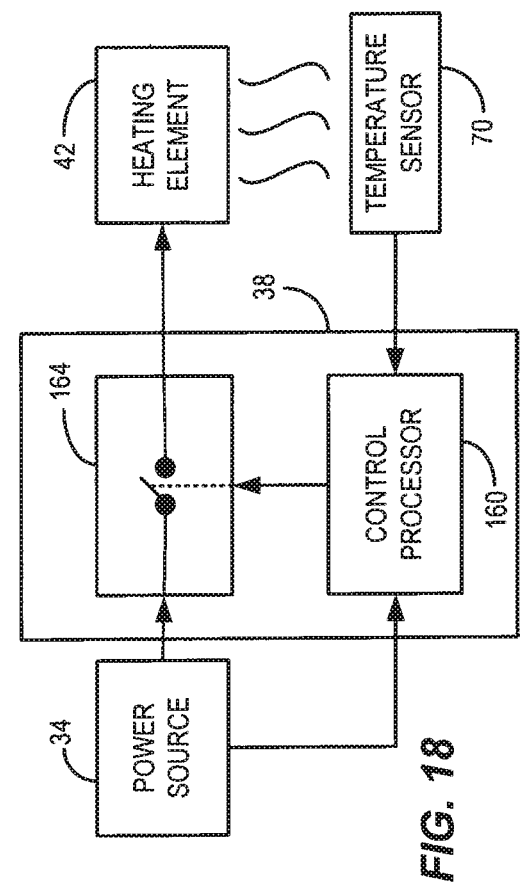
FIG. 19
FIG. 18

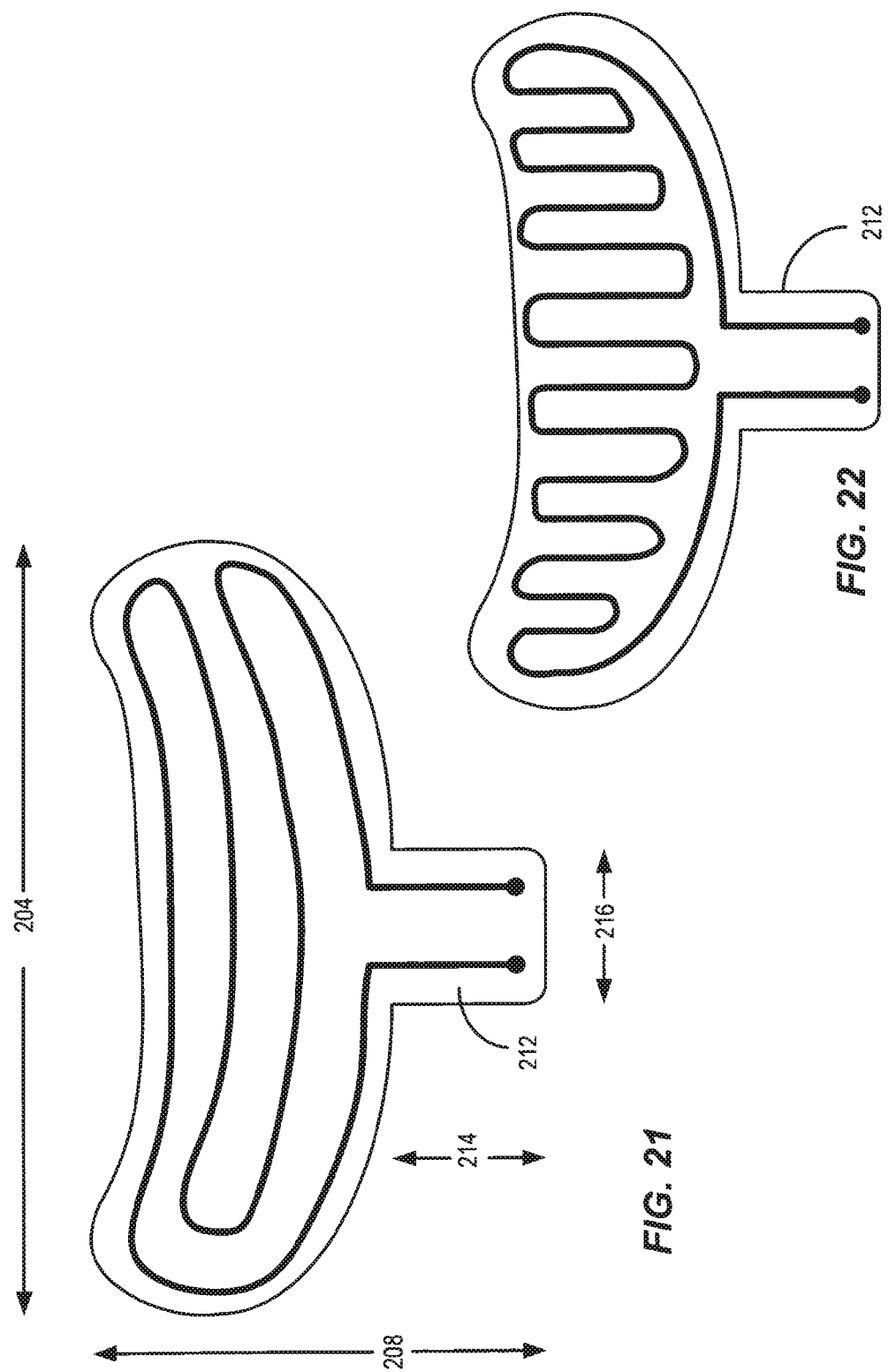

MELTING MEIBOMIAN GLAND OBSTRUCTIONS

CROSS REFERENCE TO RELATED DOCUMENTS

This application is a Divisional application of U.S. patent application Ser. No. 11/541,308, filed Sep. 29, 2006 and entitled "Melting Meibomian Gland Obstructions" to Grenon et al., now published as U.S. Patent Application Publication Number 2007/0060988, which is a Continuation-In-Part application of U.S. patent application Ser. No. 11/434,054, filed May 15, 2006 and entitled "Method and Apparatus for Treating Meibomian Gland Dysfunction" to Korb, et al., now issued as U.S. Pat. No. 8,083,787, which claims priority benefit of U.S. Provisional Application No. 60/700,233, filed Jul. 18, 2005, each of which being hereby incorporated by reference in its entirety.

This application is also related to U.S. patent application Ser. No. 11/434,033, filed May 15, 2006 entitled "Method and Apparatus for Treating Gland Dysfunction Employing Heated Medium" to Grenon, et al., now issued as U.S. Pat. No. 8,915,253, and U.S. patent application Ser. No. 11/434,446, filed May 15, 2006 entitled "Method and Apparatus for Treating Gland Dysfunction" to Korb, et al., now published as U.S. Patent Application Publication No. 2007/0016256 and abandoned, each of which being hereby incorporated by reference in its entirety.

COPYRIGHT NOTICE

A portion of the disclosure of this patent document contains material which is subject to copyright protection. The copyright owner has no objection to the facsimile reproduction of the patent document or the patent disclosure, as it appears in the Patent and Trademark Office patent file or records, but otherwise reserves all copyright rights whatsoever.

FIELD

This invention relates generally to treatment of mammalian eyes. More particularly, this invention relates to application of regulated heating of the eyelids for therapeutic purposes including, but not limited to, relieving or assisting in relieving obstruction of meibomian glands by use of heat to melt certain obstructions.

BACKGROUND

The human body contains a number of glands including the lacrimal and meibomian glands of the eye, the sebaceous or pilo-sebaceous hair glands on the face and underarms, and the mammary glands in the breasts. These glands may malfunction due to age, irritation, environmental conditions, cellular debris, inflammation, hormonal imbalance and other causes. One common disease state of the eyelid glands is the restriction or stoppage of the natural flow of fluid out of the gland caused by an obstruction.

In the human eye, the tear film covering the ocular surfaces is composed of three layers. The innermost layer in contact with the ocular surface is the mucus layer comprised of many mucins. The middle layer comprising the bulk of the tear film is the aqueous layer, and the outermost layer is a thin (less than 250 nm) layer comprised of many lipids known as "meibum" or "sebum". The sebum is secreted by the meibomian glands, enlarged specialized sebaceous-type glands (hence, the use of "sebum" to describe the secretion) located on both the upper and lower eye lids, with orifices designed to discharge the lipid secretions onto the lid margins, thus forming the lipid layer of the tear film. The typical upper eyelid has about 25 meibomian glands and the lower eyelid has about 20 meibomian glands, which are somewhat larger than those located in the upper lid. The meibomian gland comprises various sac-like acini which discharge the secretion into the main central duct of the gland. The secretion then passes into the orifices which are surrounded by smooth muscle tissue and the muscle of Riolan which are presumed to aid in the expression of sebum. The meibomian gland orifices open onto the lid margin at and around the junction of the inner mucous membrane and the outer skin of the eyelids termed the mucocutaneous junction.

Specifically, as illustrated in the above patent applications, each meibomian gland has a straight long central duct lined with four epithelial layers on the inner surface of the duct. Along the length of the central duct there are multiple lateral out-pouching structures, termed acini where the secretion of the gland is manufactured. The inner lining of each acinus differs from the main central duct in that these specialized cells provide the secretions of the meibomian gland. The secretions flow from each acinus to the duct. While it has not been established with certainty, there appears to be a valve system between each acinus and the central duct to retain the secretion until it is required, at which time it is discharged in to the central duct. The meibomian secretion is then stored in the central duct and is released through the orifice of each gland onto the lid margin. Blinking and the squeezing action of the muscle of Riolan surrounding the meibomian glands are thought to be the primary mechanism to open the orifice for the release of secretion from the meibomian gland.

Blinking causes the upper lid to pull a sheet of the lipids secreted by the meibomian glands over the other two layers of the tear film, thus forming a type of protective coating which limits the rate at which the underlying layers evaporate. Thus, it will be seen that a defective lipid layer or an incorrect quantity of such lipids can result in accelerated evaporation of the aqueous layer which, in turn, causes symptoms such as itchiness, burning, irritation, and dryness, which are collectively referred to as "dry eye".

Dry eye states have many etiologies. A common cause of common dry eye states is the condition known as "meibomian gland dysfunction" (MGD), a disorder where the glands are obstructed or occluded. A common cause of common dry eye states is a disorder where the glands are obstructed or occluded, usually referred to as "meibomian gland dysfunction" (MGD). As employed herein the terms "occluded" and "obstruction" as they relate to meibomian gland dysfunction are defined as partially or completely blocked or plugged meibomian glands, or any component thereof, having a solid, semi-solid or thickened congealed secretion and/or plug, leading to a compromise, or more specifically, a decrease or cessation of secretion. Also with a reduced or limited secretion the meibomian gland may be compromised by the occluded or obstructive condition as evidenced by a yellowish color indicating a possible infection state, or may be otherwise compromised so that the resulting protective lipid protective film is not adequate.

Meibomitis, an inflammation of the meibomian glands leading to their dysfunction, is usually accompanied by blepharitis (inflammation of the lids). Meibomian gland dysfunction may accompany meibomitis, or meibomian gland dysfunction may be present without obvious lid inflammation. Meibomian gland dysfunction is frequently the result of keratotic obstructions which partially or completely block the meibomian gland orifices and/or the central duct (canal) of the gland, or possibly the acini or acini valves (assuming they do in fact exist) or the acini's junction with the central duct. Such obstructions compromise the secretory functions of the individual meibomian glands. More particularly, these keratotic obstructions can comprise combination of bacteria, sebaceous ground substance, dead, and/or desquamated epithelial cells, see, Korb et al., Meibomian Gland Dysfunction and Contact Lens Intolerance, Journal of the Optometric Association, Vol. 51, Number 3, (1980), pp. 243-251. While meibomitis is obvious by inspection of the external lids, meibomian gland dysfunction may not be obvious even when examined with the magnification of the slit-lamp biomicroscope, since there may not be external signs or the external signs may be so minimal that they are overlooked. The external signs of meibomian gland dysfunction without obvious lid inflammation may be limited to subtle alterations of the meibomian gland orifices, overgrowth of epithelium over the orifices, and pouting of the orifices of the glands with congealed material acting as obstructions. In severe instances of meibomian gland dysfunction without obvious lid inflammation the changes may be obvious, including serrated or undulated lid margins, orifice recession and more obvious overgrowth of epithelium over the orifices, and pouting of the orifices.

Hormonal changes, which occur during menopause, and particularly changing estrogen levels, can result in thickening of the oils secreted by the meibomian glands which results in clogged gland orifices. Further, decreased estrogen levels may also enhance conditions under which staphylococcal bacteria can proliferate. This can cause migration of the bacteria into the glands, thus resulting in a decreased secretion rate.

When the flow of secretions from the meibomian gland is restricted due to the existence of an obstruction, cells on the eyelid margin have been observed to grow over the gland orifice thus further restricting sebum flow and exacerbating the dry eye condition. Additional factors which may cause or exacerbate meibomian gland dysfunction include, age, disorders of blinking, activities such as computer use which compromise normal blinking, contact lens wear and hygiene, cosmetic use, or other illness, particularly diabetes.

The state of an individual meibomian gland can vary from optimal, where clear meibomian fluid is produced; to mild or moderate meibomian gland dysfunction where milky fluid or inspissated or creamy secretion is produced; to total blockage where no secretion of any sort can be obtained (see Korb, et al., "Increase in Tear Film Lipid Layer Thickness Following Treatment of Meibomian Gland Dysfunction", Lacrimal Gland, tear Film, ad Dry Eye Syndromes, pp. 293-298, Edited by D. A. Sullivan, Plenum Press, New York (1994)). Significant chemical changes of the meibomian gland secretions occur with meibomian gland dysfunction and consequently, the composition of the naturally occurring tear film is altered, which in turn, contributes to ocular disease which is generally known as "dry eye".

While the tear film operates as a singular entity and all of the layers thereof are important, the lipid layer, which is secreted from the meibomian glands, is of particular significance as it functions to slow the evaporation of the underlying layers and to lubricate the eyelid during blinking which prevents dry eye.

Thus, to summarize, the meibomian glands of mammalian (e.g., human) eyelids secrete oils that prevent evaporation of the tear film and provide lubrication to the eye and eyelids. These glands can become blocked or plugged by various mechanisms leading to so-called "dry eye syndrome". While not the only cause, meibomian gland dysfunction (MGD) is known to be a major cause of dry eye syndrome. The disorder is characterized by a blockage of some sort within the meibomian glands or at their surface preventing normal lipid secretions from flowing from the meibomian glands to form the lipid layer of the tear film.

Such secretions serve to prevent evaporation of the tear film and lubricate the eye and eyelids, hence their absence can cause dry eye syndrome. Obstructions or occlusions of the meibomian glands may be present over or at the orifice of the gland, in the main channel of the gland which may be narrowed or blocked, or possibly in other locations including the passages from the acini to the main channel.

It has been theorized that the acini of the glands may have valves at their junction with the main channel of the gland. The inventors theorize that if these valves exist, they may also become obstructed in some instances leading to reduced or blocked flow from the acini. These obstructions or occlusions may have various compositions.

In response to the foregoing, various treatment modalities have been developed in order to treat the dry eye condition, including drops which are intended to replicate and replace the natural tear film, pharmaceuticals which are intended to stimulate the tear producing cells, and various heating devices which are designed to assist in unclogging the meibomian glands. Other techniques involve manual expression of the glands.

Eye drops such as Refresh®, Soothe® and Systane® brand eye drops are designed to closely replicate the naturally occurring healthy tear film. However, their use and administration is merely a treatment of symptoms and not of the underlying cause. Further, the use of drops is generally for an indefinite length of time and consequently, extended use can become burdensome and costly.

Pharmaceutical modalities such as the use of tetracycline have also been suggested to treat meibomian gland dysfunction and one such treatment is disclosed in United States Patent Publication no. US2003/0114426 titled "Method for Treating Meibomian Gland Disease", U.S. Pat. No. 6,455,583 titled "Method for Treating Meibomian Gland Disease" to Pflugfelder et al. and PCT Publication No. WO 99/58131 titled "Use of Tetracyclines for Treating Meibomian Gland Disease". However, this treatment has not proven to be universally clinically effective, and it may be unnecessary in cases where meibomian gland dysfunction is the result of obstruction of the gland without infection. The use of corticosteroids have also been proposed to treat meibomian gland dysfunction as disclosed in U.S. Pat. No. 6,153,607 titled "Non-preserved Topical Corticosteroid for Treatment of Dry Eye, filamentary Keratitis, and Delayed Tear Clearance (or Turnover) to Pflugfelder et al. Again, this proposed treatment appears to treat the symptom of dry eye, as opposed to treatment of the underlying cause. Additionally, the use of topically applied androgens or androgen analogues have also been used to treat acute dry eye signs and symptoms in Keratoconjuctivitis Sicca as disclosed in U.S. Pat. Nos. 5,958,912 and 6,107,289 both titled "Ocular Therapy in Keratoconjunctivitis Sicca Using Topically Applied Androgens or TGF-ß" and both issued to Sullivan.

Most knowledgeable doctors agree that heat is beneficial in treating MGD. Depending upon the nature of the obstruction, heat may be beneficial in actually melting or loosening the obstructing material, permitting the gland to begin production and excretion of lipids and other fluids more freely. However, no good method of applying localized heat to the eyelids and controlling the amount of heat applied is presently commercially available.

One modality for the heat treatment of meibomian gland dysfunction is disclosed in European Patent Application serial no. PCT/GB2003/004782 titled "Eyelid Margin Wipes Comprising Chemical Means for Temperature Adjustment". As disclosed in this patent application, a wipe is provided wherein prior to use, a chemical agent is activated that will heat the wipe to about 32° C. to about 40° C. The hot wipe is then applied to the lids and manual expression can then be used to unclog the ducts. This method is not without its drawbacks in that lid irritation can be exacerbated by non-specific heating.

Another method of heating the eyelids and meibomian glands uses near infrared (NIR) radiation. More specifically, two hard eye patches were attached to an eye mask according to the pupillary distance of the subject. The eye mask was held in place by an elastic headband. Each patch employed 19 light emitting diodes, emitting near infrared radiation from 850 nm to 1050 nm, with a peak at 940 nm. The device produced 10 mW/cm$^2$ of energy operating on electrical power. Goto, E., et al., Treatment of Non-Inflamed Obstructive Meibomian Gland dysfunction by an Infrared Warm Compression Device, British Journal of Ophthalmology, Vol. 86 (2002), pp. 1403-1407. This device is designed as a non-contact infrared heating mask using IR light emitting diodes. However, there are many potential problems with use of an IR heating mechanism. For example, the IR Heat can penetrate beyond the eyelid into the cornea which is undesirable, and could ultimately cause cataracts or other damage. Additionally, the IR mask heater places no pressure whatsoever on the eyelid (despite the description as a compression device) which we have determined is useful to expel the blockage. Moreover, tests conducted on a sample of this mask revealed that in spite of the potential dangers, the mask produced very little actual heat.

United States Patent Publication US2004/0237969 titled "Therapeutic Eye and Eye Lid Cover" comprises a pair of goggles that are adapted to deliver heated saturated air to the eyelids and particularly to the meibomian glands, again to heat the gland. Heat treatment of the eyes is also discussed in the article titled "Tear Film Lipid Layer Thickness and Ocular Comfort after Meibomian Therapy via Latent Heat with a Novel Device in Normal Subjects by Mitra et al, published in *Eye*, (2004) at pages 1-4.

United States Patent Publication US2003/0233135 titled "Method and Apparatus for Preventing and Treating Eyelid Problems" to Yee attempts to clear the plugged meibomian glands by means of electrical stimulation of the muscle of Riolan which the invention presumed to aid in the expression of the meibomian gland secretion.

SUMMARY OF CERTAIN EMBODIMENTS

It is an object of certain embodiments consistent with the present invention to provide a method and/or apparatus for regulated, selective heating of mammalian eyelids.

It is another object of certain embodiments consistent with the present invention to provide a method and/or apparatus suitable for heating meibomian glands of the upper and/or lower eyelids of either or both eyes in order to aid in the clearing of certain types of obstructions that may be present in or about the meibomian glands.

In one embodiment consistent with the present invention, an apparatus that provides regulated heat for treatment of a mammalian eyelid has a heater unit having a heating element that produces heat when electrical signal is applied thereto. A temperature regulator applies the electrical signal to the heating element in order to achieve heating of the heating element to a specified temperature range. An eyelid interfacing mechanism couples the heater unit to the eyelid to achieve regulated heating of the eyelid within the specified temperature range.

An apparatus that provides regulated heat to at least one of a patient's eyelids, in a manner consistent with another embodiment, has a heater unit, and the having: a heating element having first and second surfaces that produces heat when an electrical signal is applied thereto; a thermal heat sink, coupled to the first surface of the heating element in order to transfer heat from the heating element to the eyelid; an insulator coupled to the second surface of the heating element in order to reduce heat loss from the second surface; and a back plate that couples to the insulator. A temperature regulator applies the electrical signal to the heating element in order to achieve heating of the heating elements to a specified temperature range. Goggles suitable for attaching to the patient's head and covering the eyelid of the patient with a lenspiece are provided with the lenspiece having a threaded aperture therein. A threaded shaft passes through the threaded lenspiece and coupled to the heater unit at the back plate so that the heater unit can be moved into contact with the eyelid by screwing the shaft into the aperture until contact with the eyelid is achieved.

In another embodiment, an apparatus that provides regulated heat to at least one of a patient's eyelids has a heater unit has a heating element that produces heat that is transferred to the patient's eyelid when electrical signal is applied thereto. A temperature regulator applies the electrical signal to the heating elements in order to achieve heating of the heating elements to a specified temperature range. In certain preferred embodiments, the heating element is a resistive heating element.

Many variations in these embodiments are possible including, but not limited to providing a sensor that senses temperature and provides temperature information to the temperature regulator. In certain embodiment the eyelid interfacing mechanism comprises goggles that are adjustably coupled to the heater unit in order to move the heater unit to achieve contact with the eyelid. The goggles may be adjustably coupled to the heater unit by a threaded connection so that a position of the heater unit can be adjusted by a threading action. In certain embodiments, the heater unit has a thermal heat sink, coupled to a surface of the heating element in order to transfer heat from the heating element to the eyelid. The thermal heat sink may be, for example, at least one of a thermally conductive rubber member, a thermally conductive silicon member, an encapsulated fluid containing member, and a solid conductive member. A thermally conductive gel, cream or liquid can be placed between the heat sink and the eyelid to enhance thermal conduction from the thermal heat sink to the eyelid.

In certain embodiments, the heater unit may have an insulator coupled to a surface of the heating element in order to reduce heat loss from the heating unit in a direction other than a direction toward the eyelid. The thermal insulator may be one of a non-thermally conductive foam element, a non-thermally conductive rubber element, and a non-thermally conductive solid element in certain embodiments. The temperature regulator may apply a pulse width modulated electrical signal to the heating element in order to regulate the heat produced thereby, and the pulse width modulated electrical signal may be produced under control of the control processor.

In certain embodiments, the temperature regulator may incorporate a switch that selectively applies the electrical signal to the heating element in order to regulate the heat produced thereby. The electrical signal may be at least one of a current and a voltage that is selectively applied to the heating element under control of a control processor. The heater unit may have a flexible portion that contacts the eyelid in order to conform to the eyelid or may have a rigid portion that contacts the eyelid, and wherein the rigid portion is shaped to conform to the shape of the eyelid, or a combination thereof. The heater unit may have an adhesive for attaching the heater unit directly to the eyelid or may be attached to the eyelid by use of adhesive tape.

In certain embodiments, a user interface permits a user to establish at least one of a time and a temperature for the treatment. In certain embodiments, a mechanical energy generator generates vibration, pulsation, and/or milking action of the eyelid to stimulate secretion from the meibomian glands, wherein the vibration generator may imparts mechanical energy to the eyelid having both an amplitude and frequency.

In certain embodiments, the specified temperature range is above 37° C. and more preferably between 44° C. and 47° C. with a target temperature of about 45° C. In certain embodiments, a timer shuts off the signal to the heater element after a specified treatment time. The treatment time can be, for example, approximately 10 to 60 minutes, and preferably about 15 minutes. In certain embodiments, a pressure sensor measures a pressure with which the heater unit is applied to the eyelid.

A method of treating at least one of a patient's eyelids with a regulated heat in a manner consistent with certain embodiments involves: placing a heating unit having a heating element in contact with the patient's eyelid; and applying a control signal to the heating element to generate heat at the heating element and transfer the generated heat to the eyelid for a prescribed time period.

In certain embodiments, the method may further involve removing the control signal after expiration of the prescribed time period. In certain embodiments, the method may further involve installing goggles on the patient, the goggles having an adjustable eye interface containing the heating element; and adjusting the eye interface to achieve contact with the eyelid. In certain embodiments, the method may involve taping the eyepiece to the patient's eyelid using a strip of adhesive tape. In certain embodiments, the method may involve attaching the eyepiece to the patient's eyelid using a double-sided medical adhesive tape or using another form of adhesive attachment. In certain embodiments, the heat is generated to approximately 40°-50° Celsius. In certain embodiments, vibration is applied to the patient's eyelid. In certain embodiments, the prescribed time period is approximately 10 to 60 minutes. The method can be applied to upper, lower or both eyelids of one or both eyes. In certain embodiments, the method further involves measuring a pressure with which the heating unit contacts the eyelid. A tangible computer readable storage medium may store instructions that, when executed on a programmed processor, carry out appropriate portions of any of these methods.

In certain embodiments, a method of treating a mammalian eyelid involves heating the eyelid and maintaining a prescribed temperature for at least 4 minutes and no more than 60 minutes, while simultaneously applying mechanical energy and pressure to the eyelid. In other embodiments, a method of treating at least one mammalian eyelid involves applying continuous regulated heat to the at least one mammalian eyelid for a duration no longer than 60 minutes and applying a force to the eyelid during heating or within 3 minutes following heating for the purpose of clearing meibomian gland obstructions.

The above objects and summaries are intended to illustrate exemplary embodiments which will be best understood in conjunction with the detailed description to follow, and are not intended to limit the scope or meaning of the appended claims, which should be interpreted in light of the full teachings of the entire specification and drawings. Many other variations will occur to those skilled in the art upon consideration of the present teachings which uses a plurality of exemplary, but non-limiting example embodiments.

BRIEF DESCRIPTION OF THE DRAWINGS

Certain illustrative embodiments depicting organization and method of operation, together with objects and advantages may be best understood by reference detailed description that follows taken in conjunction with the accompanying drawings in which:

FIG. 1 depicts upper and lower human eyelids showing the meibomian glands.

FIG. 2 is a cutaway view of an illustrative meibomian gland 20.

FIG. 3 is a cutaway view meibomian gland 20 illustrating several clogging mechanisms.

FIG. 4 is a graph of temperature versus time.

FIG. 5 is a graph of inner and outer eyelid temperature versus time.

FIG. 6 is a block diagram of an eyelid heating circuit consistent with certain embodiments of the present invention.

FIG. 7 is a block diagram of another embodiment of an eyelid heating circuit consistent with certain embodiments of the present invention.

FIG. 8 is a goggle assembly for providing heat therapy to an eyelid in a manner consistent with certain embodiments of the present invention.

FIG. 9 is a first embodiment of an eyelid interface assembly with a threaded interconnection to a goggle lenspiece in a manner consistent with certain embodiments of the present invention.

FIG. 10 is a cutaway view of a first embodiment of a pressure measurement mechanism used in the eyelid interface assembly in a manner consistent with certain embodiments of the present invention.

FIG. 11 is a second embodiment of a pressure measurement mechanism used in the eyelid interface assembly in a manner consistent with certain embodiments of the present invention.

FIG. 12 is a third embodiment of a pressure measurement mechanism used in the eyelid interface assembly in a manner consistent with certain embodiments of the present invention.

FIG. 13 is a second embodiment of an eyelid interface assembly with a threaded interconnection to a goggle lenspiece in a manner consistent with certain embodiments of the present invention.

FIG. 14 illustrates an eyelid heating assembly consistent with certain embodiments of the present invention.

FIG. 15 illustrates another eyelid heating assembly consistent with certain embodiments of the present invention.

FIG. 16 is another eyelid heating assembly consistent with certain embodiments of the present invention.

FIG. 17 is an example of one embodiment of an eyelid heating assembly incorporating a vibrator in a manner consistent with certain embodiments of the present invention.

FIG. 18 is a block diagram of a heating element control arrangement consistent with certain embodiments of the present invention.

FIG. 19 is a block diagram of another heating element control arrangement consistent with certain embodiments of the present invention.

FIG. 21 illustrates an embodiment of a heating element consistent with certain embodiments of the present invention.

FIG. 22 illustrates another embodiment of a heating element consistent with certain embodiments of the present invention.

DETAILED DESCRIPTION

Figure 20:
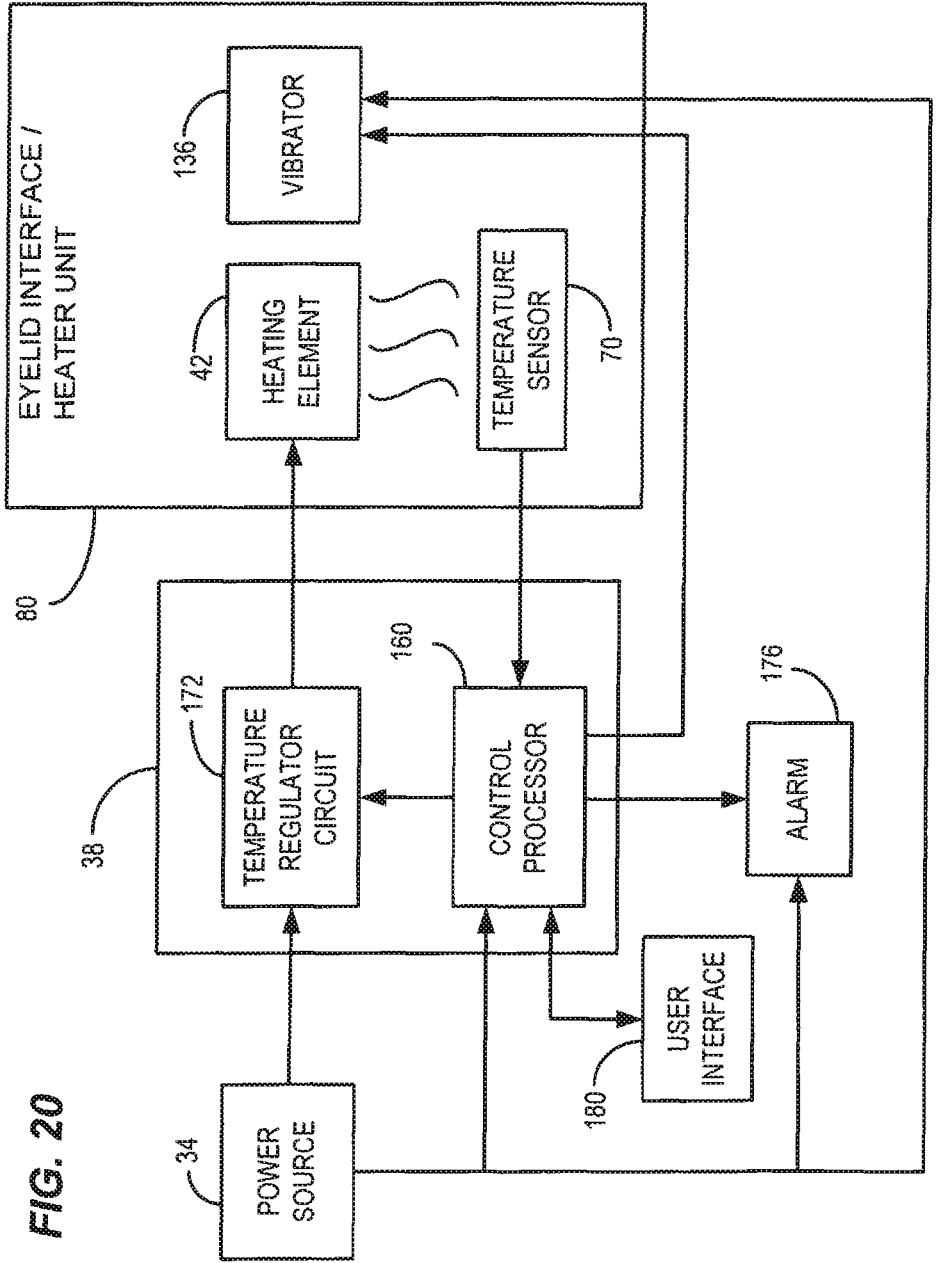
FIG. 20 is a block diagram of another heating element control arrangement incorporating vibrator control in a manner consistent with certain embodiments of the present invention.

While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically. The term "program" or "computer program" or similar terms, as used herein, is defined as a sequence of instructions designed for execution on a computer system. A "program", or "computer program", may include a subroutine, a function, a procedure, an object method, an object implementation, in an executable application, an applet, a servlet, a source code, an object code, a shared library/dynamic load library and/or other sequence of instructions designed for execution on a computer system.

Reference throughout this document to "one embodiment", "certain embodiments", "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means "any of the following: A; B; C; A and B; A and C; B and C; A, B and C". An exception to this definition will occur only when a combination of elements, functions, steps or acts are in some way inherently mutually exclusive.

As noted above, meibomian gland dysfunction (MGD) is known to be a major cause of dry eye syndrome. The disorder is characterized by a blockage of some sort within the meibomian glands preventing normal lipid secretions from flowing. Obstructions or occlusions of the meibomian glands may be present over or at the orifice of the gland, in the main channel of the gland which may be narrowed or blocked, or possibly in other locations including the passages from the acini to the main channel.

It has been theorized that the acini of the glands may have valves at their junction with the main channel of the gland, and that these valves may be obstructed in some instances leading to reduced or blocked flow from the acini. These obstructions or occlusions may have various compositions.

Referring now to FIG. 1, the location of the meibomian glands 10 are shown on the upper and lower eyelids 12 and 14 respectively. As briefly stated herein above, the upper lid contains about 25 meibomian glands and the lower lid contains about 20 meibomian glands, with significant variation. As shown in cross-sectional view of one gland 10 in FIG. 2, each gland includes a central duct or channel 18 into which the secretion flows from acini 19 and an orifice 20 which opens on to the eyelid margin and through which the secretion flows in order to be added to the tear film upon blinking. It will be seen that the glands are of different size, depending upon the location in the eyelid and that the orifice 20 is narrower than the central duct 18. The orifice is an opening and not a duct or channel. The orifice is usually shut—the orifice or opening is like other openings that pass fluids or secretions and remains closed until opened for discharge. Thus technically the duct proximal to the orifice is narrower than in the main channel.

Obstruction composition will vary with the etiology which produced it. However, the obstruction will, in most cases observed to the present, be a combination of, dead cells, bacteria, desquamated cells, desquamated cells aggregating in keratotic clusters, milky fluid, inspissated or creamy secretions, or any combination of the foregoing in solid, semi-solid and thickened forms. Referring to FIG. 3, a simplified view of exemplary obstructions to gland 10 are depicted. In this example, which is by no means necessarily representative of all meibomian gland obstructions, as explained above, a solid or semi-solid or thickened plug 24 is depicted which is fully occluding the duct leading to orifice 20 of gland 10. Another obstruction 26 is shown at a junction from one of the acini with the central duct. As previously noted, this may be the site of a valve in the gland structure, but embodiments consistent with the present invention should not be limited by theories of the actual meibomian gland structure.

A number of treatment techniques have been proposed to restore these glands to normal functionality, but most doctors agree that heat is beneficial in treating MGD. Depending upon the nature of the obstruction, heat may be beneficial in actually melting or loosening the obstructing material, permitting the gland to begin production and excretion of lipids and other fluids more freely. However, no good method of applying localized heat to the eyelids and regulating the amount of heat applied has been available.

One treatment method for applying heat to the eyelids is the use of warm water compresses. Alternatively, small thermal masses (e.g., rice or flax seed) can be used by placing material into jackets much like a bean bag. These bean bags can then be heated in a microwave and applied to the eyelid.

These techniques are not fully satisfactory in applying localized heat to the eyelid. Hot compresses are large in size relative to the eyelid. They are also messy, uncontrolled, and time consuming. Moreover, their large size results in heating areas surrounding the eyelids which make the process uncomfortable and possibly messy and even counterproductive.

It is also theorized that localized heating of the eyelid alone would be more beneficial than heating both the eyelid and the face surrounding the eyelids. By heating the areas outside the eyelids, more blood vessels in the face will become dilated and the blood flow to the eyelid and surrounding areas will theoretically be increased. Unfortunately, this added blood flow will tend to reduce the temperature of the eyelid by means of thermal convection through the blood stream. This is the body's natural attempt to regulate the temperature of the eyelid. Since it is desirable to keep the eyelid at a constant therapeutic temperature that is higher than normal body temperature, it follows that heating a large area is potentially counterproductive because more vessels will be dilated and more blood will be flowing, thus requiring even more heat to raise the temperature.

By their very nature, hot compresses and bean bags do not have good temperature control. Therefore, from patient to patient and application to application, the temperature of these compresses will vary. This can potentially be hazardous or uncomfortable to the patient if the temperature is too hot and ineffective if the temperature is too low. To make matters worse, the compresses begin cooling as soon as they are placed on the eyelid and may stay in the therapeutic temperature range for only a short period of time before becoming ineffective and perhaps even serving to draw heat from the eyelid.

One way to get around the messiness is to use small conformal thermal masses which are placed inside a "bean bag" and heated in a microwave oven. One example is the use of rice placed in a cloth bag for this purpose. While this is less messy than hot compresses, it is also less effective because the heat transfer in dry heat is much lower than wet heat. This is due the fact that air trapped between the heater and the surface being heated acts as an insulator compared to a fluid boundary which provided very good heat transfer. Additionally, because these devices depend upon the thermal mass of the device for heat transfer, the smaller the device is the less heat can be drawn from the device. Hence, by definition, any device which is heated prior to application needs to have a fairly large size in order to provide the thermal mass needed to raise the eyelid temperature before it cools down substantially.

In accordance with certain embodiments, it is preferable that the surface applied to the eyelid have a characteristic which maintains a film of moisture between the heating device and the eyelid. Thus, the heat sink preferably maintains moisture at the eyelid interface to further facilitate heat transfer to the eyelid.

FIG. 4 illustrates this problem in the form of a graph of temperature versus time. The therapeutic temperature range has been determined to be greater than 37° C. A range of approximately 44° C. to 47° C. is most preferable since temperatures approaching 50° C. generally becomes difficult for a human to endure and may cause unnecessary pain or minor burns. A proposed target treatment temperature is 45° C. as indicated by curve 25 (which provides a good balance between comfort and efficacy). Curve 25 illustrates a relatively constant 45° treatment temperature for a specified treatment time (e.g., for embodiments consistent with the present invention, 10-20 minutes is preferred, with 15 minutes currently being considered a good specified time for most patients exhibiting mild to moderate MGD. For more severe MGD, between approximately 30 to 45 minutes has been found more effective. For extremely severe MGD, approximately 30 to 60 minutes is more effective. These times are for a temperature of approximately 45 degrees C., and may potentially be increased or decreased at other temperatures. In tests, ranges between 10 and 60 minutes are generally effective.

When hot compresses or bean bag devices are used, the results will appear something like curves 28 and 30 where curve 28 may start out higher than the therapeutic temperature range and possibly at an uncomfortable temperature level, which may even cause injury, and immediately begins to drop in temperature quickly falling below the therapeutic temperature range. When the compresses are deemed to be too cool, a new compress or bean bag is used resulting in a short time gap as the heat source is changed and then to temperature curve 30. Again, this curve may start out above the therapeutic temperature range and ultimately falls to below the therapeutic temperature range. Test measurements of lid temperature rise time while heated with a continuous regulated heat source as shown in FIG. 5 shows that a hot compress or beanbag device would need to stay hot within therapeutic temperature range for at least approximately 4 minutes. If it were taken off the lid to reheat, then the lid temperature would drop back to body temperature very quickly and normally within 90 seconds (possibly within 30 seconds or so), thus requiring the hot compress to start heating the lid all over again. Clearly this method is highly inefficient and has little chance of raising and maintaining the eyelid temperature to the higher therapeutic level required.

A number of treatment techniques have been proposed to restore these glands to normal functionality, but most doctors agree that heat is beneficial in treating MGD. Depending upon the nature of the obstruction, heat may be beneficial in actually melting or loosening the obstructing material or material binding solid particles to form the obstruction, permitting the gland to begin production and excretion of lipids and other fluids more freely. While the heat treatment methods described in the Background section hereof have been found to have many drawbacks, the heating techniques described in the above referenced copending applications have been found effective and beneficial. Generally speaking, these devices produce a regulated heating of the eyelid (as measured at the outer surface thereof) to a therapeutic temperature of between 40 and 50 degrees Celsius, and more preferably between about 44 and 47 degrees Celsius with a target temperature of 45 degrees Celsius.

The outside skin surface of the human eyelid has been observed to be approximately 1-2 degrees Celsius cooler than body temperature, with some variation. Increasing the temperature to at least 37 can begin to provide therapeutic effect for milder cases of MGD. One preferred range for treatment is 44 to 47 degrees Celsius, with a target of 45 degrees Celsius has been found effective and comfortable to the patient. In certain embodiments, the mechanical treating is carried out during or immediately after the end of the time period, and preferably with a heated instrument so as to maintain the more fluid state of the obstruction. Even higher temperatures (e.g., 50-55 degrees Celsius) can be used (or pulsed for short periods), especially if the eyelid has been anesthetized, in which case much hotter treatment for shorter time can be used without permanent injury to the patient. Generally, higher temperatures can be used for shorter periods of time. Moreover, the temperature and time used should be individualized based on the severity of the condition and the tolerance of the patient. It has been found that lighter skinned patients can generally tolerate less heat than darker skinned patients, and darker skinned patients tend to exhibit less inflammation as a result of exposure to the heat. Treatment times and/or temperature can be adjusted to account for these differences. Each of the above temperatures refer to the temperature as measured at the outer surface of the eyelid.

Also, in certain embodiments, the patient is more comfortable when the treatment begins at a lower temperature and the temperature is raised over time. Hence, the temperature should be regulated, where regulation should be interpreted to mean the amount of continuous heat can be increased and/or decreased and delivered to the eyelid in an automated, controlled and repeatable manner. Hence, additional heat can be applied at will. The temperature profile for heat application may be a constant temperature, or may have ramp-ups, ramp-downs, peaks, valleys, can be pulsed, or can be modulated with various characteristics, etc., but such profile should be regulated so as to be repeatable. It has also been found that modulating the temperature can result in a higher average temperature than a constant temperature, and may be useful in some applications.

This temperature can be maintained at a therapeutic temperature for a treatment period of approximately 10-60 minutes (or even beyond have been found safe and useful for some patients). Either during or after such treatment by regulated heat, mechanical expression of lipids and other fluids from the meibomian glands has been found to clear obstructions which have essentially melted or been placed in a suspension state (by virtue of melting materials binding solids together). The above applications disclose devices which generally apply a milking action to the eyelid to express the fluids or suspensions or to otherwise mechanically stimulate the movement of fluids from the glands—such fluid now including melted or suspended materials causing the obstructions or occlusions. In some instances, just gentle continuous force applied to the eyelid will assist in expression of the fluids and suspensions, while in others vibration can be used simultaneously or immediately after the heating. For purposes of this document, the terms "melted" is to be interpreted to be inclusive of states in which solid particles remain suspended within a liquid fluid.

Referring now to FIG. 5, a graph depicts the inner surface of an eyelid and an outer surface of an eyelid when a source of constant heat at about 45 degrees C. was applied to an example subject patient. The heater is turned on at time 0:00 and off at time 8:00 (eight minutes later). It should be noted that the circulatory system attempts to regulate the temperature of the eyelid, and blood flow increases with the application of heat. For this patient, it took approximately 4 minutes for the eyelid's outer surface to reach about 45 degrees Celsius, and the inner surface of the eyelid never reached this temperature—presumably because of the body's heat regulatory mechanisms. Hence, if a 45 degree constant heat source is used, it may take at least 4 minutes for the eyelid to reach a therapeutic temperature.

It is also noted from this graph, that when the heat source is removed from the eyelid, the temperature drops very quickly to body temperature. In virtually all cases, this temperature will drop within 2-3 minutes, but more commonly, only about 30 seconds to 90 seconds are required for the patient's eyelid temperature to drop. In this example, the temperature dropped very quickly over the first thirty seconds after removal of the heat. During this short time period, some or all of the melted obstruction may re-solidify. Hence, if manual expression techniques are to be carried out subsequent to application of heat, the manual expression should follow immediately, or within about 90 seconds—with shorter intervals being preferred, e.g., within 30 seconds. It will thus be clear from this graph that prior techniques of using warm compresses may be substantially less effective if manual expression does not follow within an extremely short period of time. Moreover, if the compresses do not maintain their heat within a therapeutic range for at least 4 minutes or cool below a therapeutic level prior to manual expression, they may provide minimal benefit to a patient suffering from substantial obstruction.

FIG. 6 is a block diagram depicting treatment of the meibomian glands of the eyelid, and in particular the lower eyelid, as illustrated. It is noted that this treatment (as well as the other treatments described and apparatus described herein) can be utilized or adapted for either the upper or lower eyelid, or both upper and lower eyelid for either left or right eye or both left and right eyes. In this embodiment, a power supply 34 supplies power to a heat regulating circuit 38, which may be of any suitable design to provide heat regulation. This heat regulating circuit 38 applies an electrical signal such as a current (AC, DC, pulsed, programmed or modulated) to heating element 42 (e.g., a flexible foil heater element that produces heating by virtue of the heat produced when current passes through a resistor, i.e., resistive heating) in order to produce a regulated temperature within the therapeutic range, for example at about 45° C. This heating element 42 is used to generate the heat which ultimately is transferred to the eyelid for heat therapy. In the present embodiment, a heat sink 46 is disposed between the heating element 42 and eyelid 50 of eyeball 54. This heat sink 46 may be either, for example, a flexible silicon member that flexes (along with the heating element in some embodiments) to conform to the shape of the eyelid being treated. In one embodiment, a flexible silicone rubber pad that is relatively thermally conductive (e.g., one or two layers ¹⁄₁₆ inch thick) can be used. Alternatively, the heat sink 46 may be a rigid or relatively rigid thermally conductive member which is pre-shaped to closely conform to the outer surface of the eyelid 50. In this embodiment, one typical size or multiple sizes may be provided to match the eyeball contour and provide therapy to both the upper an lower lids simultaneously, but could be readily adapted to treat a single eyelid of a single eye or both eyelids of a single eye, or a single eyelid of both eyes or both eyelids of both eyes.

The heating element 42 is sandwiched between this heat sink 46 and insulator 58. Insulator 58 serves to minimize heat loss from the back side of the heating element (the side furthest from the eyelid being treated) and thereby assists in channeling heat from the heating element 42 through the heat sink to the eyelid 50. In certain embodiments, a backing plate 62 is optionally applied to the outer surface of the thermal insulator 58 in order to assist in attaching the assembly to the eyelid or otherwise contacting and engaging the eyelid 50, as will become clear later. In certain embodiments, a slight force illustrated by arrow 66 urges the heat sink into close contact with the eyelid 50 in order to more efficiently transfer thermal energy to the eyelid while also applying force to the meibomian glands to urge them to expel fluids.

One of the reasons for using heat to treat the meibomian glands is that it has been observed that heating the meibomian glands causes materials which are causing obstructions and occlusions to essentially melt and become fluid. Thus, the heat is beneficial and the slight pressure urges the melted material that was causing the obstructions to be expelled from the meibomian gland or glands. For purposes of this document, the term "melted" is to be interpreted to be inclusive of states in which solid particles remain suspended within a liquid fluid.

In accordance with certain embodiments, the heating element 42 is realized as a flexible foil resistive heating element. Such elements comprise a flex-circuit having resistive pathways through which electrical current is passed to cause generation of resistive heat. In such heating elements, the temperature can often be monitored by measurement of the resistance of the element—which changes somewhat as the element heats up. Resistance can be measured in a number of ways including indirectly by measuring the current flow to the heating element and/or the voltage applied across it. Hence, in such heating elements as used in this particular embodiment, the primary or only mode of heat production is via direct contact of the heating unit with heat provided by resistive heating and production of potentially harmful infrared light energy is minimal or nonexistent. Other types of resistive heating elements may also be used without departing from embodiments consistent with the present invention.

The circuit depicted in FIG. 6 is basic in nature and may utilize many variations consistent with embodiments of the present invention. In one embodiment, a fixed temperature device such as that illustrated in FIG. 6 may be utilized in which the heat regulating circuit 38 is factory calibrated to produce the desired constant therapeutic temperature at heating element 42. This constant therapeutic temperature can be factory calibrated by measurement of the temperature and resistance of the heating element 42 or heat sink 46 so that a safe and therapeutic level of heat is obtained. A selection of heat settings can be provided for use by the clinician or patient. The heat regulating circuit may also incorporate a timer so that heat is applied for a specified period of time once the heating cycle starts, and the heat is terminated after the specified treatment time. In addition, the heat regulating circuit may trigger an alarm notifying the user of an end of the treatment period when the specified treatment time has expired. In general, a treatment time of about 15 minutes has been found to be satisfactory, but a great deal of variation and optimization may be possible without deviating from the present invention. Generally, times ranging between about 10 and 60 minutes are appropriate, depending upon severity of the condition and temperature, but this should not be considered limiting.

Additionally, the heating element may be realized as a collection or array of heating elements without limitation. Each of these variables and others will occur to those skilled in the art upon consideration of the present teachings.

For purposes of this document, the insulator is suitably insulative so as to tend to serve as a barrier to the escape of heat from the rear of the heater element, whereas, the heatsink should be suitably conductive so as to tend to draw heat from the heater element toward the eyelid. In embodiments consistent with the present invention, where contact with the human eyelid is desired, it is often desirable that the heat sink or other element placed in contact with the eyelid be soft and comfortable. This may limit the actual absolute thermal conductivity of that material. However, so long as there is a reasonable tendency for heat to flow through the material, it will be considered a heat sink. Similarly, the insulator, due to similar restrictions as well as size, is unlikely to resemble an ideal insulator, but keeping the heat adequately directed toward the eye with a reduction in heat loss over the bare heater element is adequate to be considered an insulator. The relative thermal conductivity of the heat sink should therefore be greater than the thermal conductivity of the insulator, and preferably it should be much greater (e.g., a factor of 10). That is, the insulator should preferably be less conductive of heat than the heat sink.

In prototypes, the insulator had thermal conductivity of less than that of 92% rubber, which has a thermal conductivity of approximately, 0.10 W/mK (watt per meter-Kelvin) while the heat sink had a thermal conductivity of approximately 1.3 W/mK, but these conductivity values should not be considered limiting. In certain embodiments, the back plate may serve adequately to provide the function of the insulator.

It will be appreciated by those skilled in the art that the terms "heat sink" and "thermal insulator" are relative terms that describe the tendency of a material to either absorb and transfer heat or inhibit the flow of heat. For purposes of this document, the term "heat sink" will suggest that the substance in question is a relatively good conductor of heat (compared to an insulator). For materials such as thermally conductive silicon rubber, heat conductivity is generally better than that which would be considered a thermal insulator, even though it may not be as good as a metal such as steel or aluminum. However, commercially available materials that are designed for enhanced thermal conductivity are available and are made of flexible material such as silicon rubber. Similarly, most "thermal insulators" will inherently conduct a certain amount of heat. This fact will not preclude a material from being considered a thermal insulator for purposes of this document. Thermally insulating materials such as insulating foam rubber and plastics and the like are commercially available.

One example of thermally insulating material suitable for use in embodiments of the present invention is neoprene rubber with a thickness of approximately ⅛ to ¼ inch, but these dimensions should not be considered limiting. Thermally conductive silicone rubber materials can be obtained commercially from a number of sources including, for example, Stockwell Elastomerics, Inc. of 4749 Talbut Street, Philadelphia, Pa. 19136 as product T100.

Referring now to FIG. 7, an alternative embodiment is depicted which is similar to that of FIG. 6, except for the inclusion of a separate temperature sensor 70 adjacent to heating element 42. This temperature sensor is shown for convenience as occupying a separate layer in the structure, but this is merely for convenience of illustration. Temperature sensor 70 could be placed anywhere between the insulator 58 and the heat sink 46, between the heating element 42 and the heat sink 46, between the heating element 42 and the insulator 58, embedded within the heater element 42, embedded within the heat sink, or at the surface of the eyelid without limitation, so as to read the temperature being generated by the heating element 42 and/or delivered to the outer surface of the eyelid. If the heat sink and insulator properly do their job, any of these points can be used to measure the temperature that is ultimately delivered to the outer surface of the eyelid (or can be calibrated to represent the final eyelid surface temperature) to a reasonable degree of accuracy (after a settling time period). The optimum place to measure this temperature, however, is at the surface of the eyelid.

The temperature sensor 70 may be realized as an array of sensors in certain embodiments. Temperature sensor 70 sends an electrical signal back to the regulating circuit 38 so that the heat regulating circuit 38 can monitor the actual temperature generated by heating element 42. Feedback control techniques can then be utilized so that proper heating within a therapeutic range is maintained at heating element 42. Temperature sensor 70 may be realized in a number of ways including, but not limited to, a thermocouple (e.g., the extremely small thermocouples available from Physitemp Instruments Inc. of 154 Huron Avenue, Clifton, N.J. 07013) or a conventional miniature thermistor.

Referring now to FIG. 8, one embodiment of a treatment device consistent with the present invention is depicted in which a separate housing 76 is used to house the power supply 34 and heat regulating circuit 38. This housing can be attached by wiring 78 to a heater unit 80. Alternatively, the power supply 34 and heat regulating circuit can be embedded within the goggle assembly or a helmet-like assembly. Heater unit 80 incorporates some or all of the elements described in FIGS. 6 and/or 7 (as well as variations described later) with the outer surface of heat sink 46 providing an interface to the eyelid. Heater unit 80 would incorporate the heat sink 46, heating element 42, possibly temperature sensor 70, as well as insulator 58 and backing plate 62. One or two layers of a ¹⁄₁₆ inch thick silicon rubber heat sink was used in prototypes with satisfactory results. The backing plate 62 in the present embodiment is utilized to affix a ball 84 to a captivating socket in the backing plate so that the heater unit 80 can be rotated and otherwise adjusted with respect to a holder (e.g., goggles as will be described) to appropriately contact the eyelid to be treated. The ball is in turn connected to a threaded shaft 88 which has a wing nut, thumbscrew, or other conveniently manipulated termination 92 so that the user, clinician, nurse, physician or technician can screw the shaft in to adjust the contact with the eyelid and thereby adjust the initial pressure placed on the eyelid by the heater unit. In this embodiment, the shaft is screwed through a lenspiece 94 forming a part of a goggle 98 which the user straps to the patient's head using adjustable straps 102 in a more or less conventional manner.

In certain embodiments, the heat sink, or the entire heater unit 80 or portions thereof may be made disposable so that the regulator and other parts may be re-used with multiple patients, while remaining sanitary.

For purposes of this document, goggles are used as an illustrative embodiment of a holder or interfacing mechanism that keeps the heater unit 80 in place, but other mechanisms are also possible. Thus, the use of the term "goggle" for descriptive purposes shall be considered to be any type of goggle, frame, headgear, goggle-like headgear, helmet, strap or other device that fits on a patient's head in any manner and can be utilized to hold a heater unit such as 80 in contact with a patient's eyelid during treatment as described herein. A goggle's lenspiece as discussed is defined as an element of the goggle or other device that is situated approximately where a lens would normally reside in front of the eye, and does not necessarily imply the presence of an actual optical lens.

In this embodiment, goggles similar to those used for swimming can be adapted to carry the heater unit 80 and hold it in proximity to the eyelid being treated during the specified treatment time. While the goggles 98 illustrated in FIG. 8 are more or less conventional goggles, such as those used for covering the eyes during swimming, any other suitable mechanism for holding the heater unit 80 in place at one or more of the eyelids to be treated can be utilized, including adhesives, tapes, straps, helmets, clamps or any other suitable expedient. Each such mechanism can be considered a suitable interfacing mechanism for purposes of this document.

Thus, an apparatus that provides regulated heat to at least one of a patient's eyelids, in a manner consistent with another embodiment, has a heater unit, and the having: a heating element having first and second surfaces that produces heat when an electrical signal is applied thereto; a thermal heat sink, coupled to the first surface of the heating element in order to transfer heat from the heating element to the eyelid; an insulator coupled to the second surface of the heating element in order to reduce heat loss from the second surface; and a back plate that couples to the insulator. A temperature regulator applies the electrical signal to the heating element in order to achieve heating of the heating elements to a specified temperature range. Goggles suitable for attaching to the patient's head and covering the eyelid of the patient with a lenspiece are provided with the lenspiece having a threaded aperture therein. A threaded shaft passes through the threaded lenspiece and coupled to the heater unit at the back plate so that the heater unit can be moved into contact with the eyelid by screwing the shaft into the aperture until contact with the eyelid is achieved.

In certain embodiments, an apparatus that provides regulated heat to at least one of a patient's eyelids has a heater unit having a heating element that produces heat that is transferred to the patient's eyelid when electrical signal is applied thereto. A temperature regulator applies the electrical signal to the heating elements in order to achieve heating of the heating elements to a specified temperature range.

Referring now to FIG. 9, a more detailed view of the connection of the heater unit 80 to the lens piece 94 is depicted. In this illustration, the layers of the heater unit 80 are shown in an exaggerated form in order to provide clarity. At the outermost surface is the heat sink 46 which contacts a heating element 42 which may be, for example, a flexible resistive foil heater such as those manufactured and sold by Minco Corporation. Foil heaters are readily available commercially and may be provided with size and thermal properties suitable for use in the present heating unit 80. The next layer is the insulating layer 58 which serves to prevent heat from dissipating from the rear of the heater unit 80 so that heat is maintained where it is needed in contact with the eyelid. Finally, the backing plate 62 is affixed to the backside of the insulator 58 to effect interconnection with a structure that holds the heater unit 80 in proper engagement with the eyelid. In some embodiments, the back plate described later may itself be constructed of a material that has suitable insulative properties to be considered both a back plate and an insulator.

This embodiment of backing plate 62 includes a socket 110 which receives ball 84 to permit the threaded shaft 88 to turn freely and to permit the heater unit 80 to pivot so as to be properly interfaced with the eyelid to be treated. The threaded shaft 88 passes through lenspiece 94 and is fitted in this example with a gnarled knob 114 which permits the user, patient, doctor, clinician, nurse, or technician to adjust the amount of pressure being applied to the eyelid to assure good contact, patient comfort, and proper therapeutic application of the heat—preferably with at least a small amount of pressure.

A small force sensing device or mechanism can be added to set the pressure consistently. A simple version of such a device is illustrated in partial cutaway in FIG. 10. In this exemplary embodiment, a spring or material with spring characteristics 104 is inserted between the ball 84 used in the ball joint and the threaded shaft 88. The ball 84 fits into the eyepiece socket 110 of FIG. 9, but ball 84 is now attached to a hollow tube 106 instead of directly to the threaded shaft 88. The hollow tube 106 has spring 104 inserted in the tube 106 and the threaded shaft 88 pushes against the spring 104 which in turn pushes on the ball joint, thereby urging the eyepiece against the eyelid. The amount of displacement between the hollow tube 106 and the threaded shaft 88 provides an indication of force. The hollow tube 106 may include indicia that are revealed as pressure is reduced and concealed as pressure is increased. While the embodiment shown in FIG. 10 illustrates the hollow tube 106 within a hollow end portion of the shaft 88, the shaft 88 could equally well be disposed within the hollow tube 106. In such embodiment, the end of the threaded shaft 88 may be unthreaded in order to place indicia thereupon to provide an indication of pressure. Other indicators of pressure could also be devised without departing from embodiments consistent with the present invention. Tabs can be used to captivate the tube within the shaft or vice versa as illustrated.

Force could also be measured without the use of springs by simply installing a force gauge at a suitable location—for example, on the threaded shaft 88 between the goggles and the eyepiece, or embedded within the eyepiece 80 itself. This is illustrated in an exemplary embodiment shown as FIG. 11. The force gauge 116, as illustrated, is disposed along the path that force is directed such as in a segment of shaft 88. The output signal from force gauge 116 can then be processed electronically (for example using a control processor or other processing device) and a visual image representing an amount of force (e.g., a number or a graphical indication) displayed on a display device 118).

FIG. 12 depicts yet another mechanism for measuring force that uses thin film (or other) technology which changes colors as a function of force. This can be implemented, for example, by making backplate 62 out of a clear material (perfect clarity is not required, so long as a color change can be discerned) and placing a thin film pressure sensitive membrane 122 adjacent back plate 62. The thin film membrane 122 will change colors as a function of pressure. By adjusting the device to achieve a particular color a standard or otherwise known pressure can be realized.

FIG. 13 depicts a similar configuration. However, between the insulator 58 and the heating element 42, a temperature sensor shown generically as layer 70 for ease of illustration is depicted. Temperature sensor 70 may, for example, be a thermistor or heat sensitive resistor whose resistance can be measured as an indication of the temperature generated at heating element 42. A wiring bundle 78 may carry a pair of wires to the heating element 42 and a pair of wires to the temperature sensor 70 or a common wire may be utilized for both heater 42 and temperature sensor 70 so that three-wire wiring bundle 78 may be utilized to interface with unit 76. In practice, such a temperature sensor may in fact be mounted directly to the foil heater, the insulator 58 or the heat sink 46, or embedded in the heat sink 46 or at the surface of the eye. Multiple sensors 70 or heating elements 42 may also be used to provide more degrees of freedom of control.

In accordance with certain embodiments, it is desirable for the foil heater or other heating element 42 to provide uniform heat across the surface of the thermally conductive heat sink. Some off-the-shelf heater elements may not provide uniform heating across their surface or across the surface of the eyelid being treated due to the irregular shape of the eyelid compared to many commercial heater elements which may be round, square, rectangular or oval. However, a custom designed heating element can be provided which solves this problem by changing the location of where the heater element makes electrical connection to the foil and by appropriate mechanical arrangement of the heating element. By routing power to a tab that does not form a part of the heating element, and shaping the heating element to approximate a contour of the eyelid, the temperature gradient across the heater unit 80 at the eye interface can be minimized. Preferably, the heating element is appropriately shaped to provide uniform heat across the entire eyelid with no hot spots or cold spots. The use of an appropriate thermally conducted heat sink also assists in smoothing out the temperature gradient across the heater unit 80 at its interface to the eyelid. However, in certain embodiments, the heat sink may be eliminated with an appropriately designed heater element.

In prototype heater units, a commercially available Minco brand Heaterstat™ model CT198-1001R8.00L1 temperature regulator was utilized. This device has the advantage of only needing two wires to connect to a Minco brand foil heater element and provides heating current and temperature regulation to the foil heater. This can be accomplished because the Minco brand foil heater utilized in the prototype (Minco HK5207R6.5L12A—see Minco "Thermofoil Heaters" Bulletin HS-202 which is hereby incorporated by reference) acts both as a heating element and a sensor at the same time. This foil heater measures 0.3 inches by 1.5 inches and only covered an upper portion of the lower human eyelids tested. Improved heater elements are discussed later.

In prototypes the heater was operated at a 50% duty cycle at about 3.0 volts. Higher voltages result in a lower duty cycle to achieve the same heating. As the temperature increases, the resistance of the heating element also increases. Therefore, by targeting a particular resistance value, the regulator can control the temperature of the heating element by increasing current when the temperature is too low and turning off the power when the temperature is too high. In this commercially available Heaterstat™ regulator device, temperature is regulated by applying power to the foil heater and then waiting for the temperature to drop before power is applied again in a manner similar to that used by most heater thermostats. Thus, this device provides temperature that varies within a small temperature range. With the device utilized, this temperature is within about 1° C., so this device is quite suitable for use in the present application.

It has, however, been observed that the application of the heating unit to the eyelid results in a short-term drop at the surface temperature (depicted in FIG. 4 as an upward curve at the far left as the heater unit catches up with the heat initial loss). The Heaterstat™ brand temperature regulator used in prototypes was slow to initially compensate for the additional heat dissipation caused by contact with the eyelid, because the temperature drop at the eyelid is not initially detected until the temperature drain from the heat sink reaches the heater element for detection. This problem is addressed in the improved heater elements, discussed later, by increasing the heater area and total heat output.

The power supply may be AC, DC, pulsed, programmed or a modulated signal, and in an experimental prototype, three series connected AA size commercial alkaline batteries were utilized. This provides a DC voltage of approximately 3.6 volts. Since the specified treatment time used in prototype experiments was approximately fifteen minutes, the battery life of approximately one hour is adequate to carry out three to four treatments without problems. However, other embodiments may also be utilized in order to optimize battery life or to provide a solution that utilizes AC power sources, rechargeable batteries and/or modulated, pulsed or programmed signals rather than DC.

Referring now to FIG. 14, a heating unit 80 consistent with certain embodiments is depicted in which again a layered sandwich style assembly is depicted with an insulator 58 providing a rearmost layer, a heating element 42 providing a central layer, and a thermal heat sink 46 providing a front layer which will be placed in contact with the eyelid. In this embodiment, an adhesive 120 is applied to the outer surface of the heat sink in order to affix the heater unit to the eyelid. In this example, the adhesive 120 may be in the form of a double-sided adhesive tape which has a cover that is peeled off to reveal the adhesive in order to stick the heater unit 80 to the eyelid. In the example depicted, the thermal heat sink 46 may be flexible or pliable so that when pressed in place it conforms to the shape of the eyelid to provide close contact between the thermal heat sink 46 and the eyelid. However, in other embodiments, the surface carrying the adhesive 120 may be shaped in a manner that conforms with the up and down, as well as top left and right curvature of the eyelid to be treated. In this example, thermal heat sink 46 can be rigid rather than pliable. A somewhat half-moon shape is depicted for ease of illustration, but the shape is preferably one which closely conforms to the shape of an eyelid or pair or eyelids. In particular, since the lower eyelid is generally most problematic, a suitable shape to conform to the lower eyelid is desirable.

When using any adhesive mechanism to attach the heater unit 80, it is desirable to clean and dry the surfaces to which the adhesive is applied in order to remove all body oils and the like to assure that the adhesive will stick properly. Failure to do so may result in separation of the heater unit near the edges rather than conforming with the eyes.

A similar embodiment is depicted in FIG. 15. In this embodiment, a temperature sensor 70 is embedded in a layer prior to or forming a part of thermal heat sink 46. While depicted as a layer 70, the temperature sensor may be a single element temperature sensor or may be an array of temperature sensors which detects temperature across the various segments or regions of the heating element. Additionally, while a single foil heating element has been discussed heretofore, the heating element may be realized as an array of heating elements which may be individually controlled in order to provide uniform heating across the surface of the eyelid.

FIG. 16 depicts another embodiment consistent with the present invention in which a heater unit 80, such as any of those described heretofore, can be attached to the lower eyelid by use of a strip of adhesive tape, such as a single side adhesive medical adhesive tape 130, in order to hold the heater unit 80 in contact with the upper or lower eyelid for treatment. Again, heater unit 80 is depicted as having a relatively flat but flexible contact surface which conforms to the shape of the eyelid being treated in the example illustrated. However, an eyelid conformal shape using a more rigid heat sink 46 may also be utilized without departing from embodiments consistent with the present invention.

Referring now to FIG. 17, a further embodiment is depicted in which an example vibrating element 136 is incorporated within the apparatus. While heat and gentle pressure may facilitate excretion of the melted substances causing the occlusions or obstructions of the meibomian glands, application of gentle vibration, (for example during the entire treatment period or portions thereof such as near the end of the specified treatment time, or immediately afterwards) may further induce excretion of the melted obstructive material. In this embodiment, a generic vibrator 136 is depicted as embedded within the eyepiece. Such vibrating element 136 can be of any suitable design. There are multiple mechanisms that can be utilized to provide vibratory energy to the heated eyepiece. Examples, which should not be considered limiting, are as follows:

An offset motor can be used and attached to the outer surface of the eyepiece heater 80 or shaft 88. Some such offset motors operate by having an eccentric weight attached to the shaft that causes vibration when the motor is powered. An offset motor is used in cellular telephones and beepers to alert the user. They are readily commercially available in different sizes and can operate to produce vibrations at various different frequencies and amplitudes. An appropriate frequency and amplitude can be determined by experimentation upon consideration of this teaching.

Button type vibration motors can be embedded within the eyepiece or otherwise attached in a manner operative to induce vibration.

A small motor can be placed on the screw mechanism which attaches to the mask and heater. The motor can then be used to rotate a figure eight screw causing it to move in and out. The amount of displacement in this case is fixed but the speed (frequency) can be controlled with a micro-processor unit.

A small piezoelectric motor can be used to move the screw mechanism which attaches to the mask and heater. The amount of displacement and frequency of operation can be controlled with a micro-processor unit.

The screw attachment between the goggles and the eyelid heater can be removed and replaced with a diaphragm. The diaphragm can be placed between the goggles and the eyelid heater, attached to both. A simple pulsating air pump (or fluid pump) can be used to inflate and deflate the diaphragm thus providing mechanical motion to the eyelid heater. The amount of air and frequency of pulses can be controlled by a microprocessor unit.

Other embodiments wherein mechanical energy, (where mechanical energy is defined as any form of mechanical pressure on the glands to apply pressure to the meibomian gland to assist in pushing the blockage or obstruction out of the gland while the obstruction is softened by heat) energy is applied using any suitable mechanism can be devised upon consideration of the present teachings. Once the heating element has served to melt the obstructions of the meibomian gland or glands, application of mechanical energy such as pulsing, vibratory energy, milking, etc. action to the eyelid will stimulate the excretion of lipids along with the now fluidic material that once constituted the obstruction.

Referring now to FIG. 18 one mechanism for regulation of the temperature generated by heating element 42 is depicted. In this embodiment, heat regulating circuit 38 is implemented by use of a control processor 160 which received feedback information from temperature sensor 70 and utilizes this information to control a switch 164 that applies power to the heating element 42 in order to regulate the temperature of the heating element 42. While this embodiment depicts the heating element 42 and temperature sensor 70 as being two separate devices, as previously indicated, the resistance of the heating element or other characteristics of the heating element 42 can also be utilized for purposes of sensing the operational temperature of the heating element(s). Control processor 160 operates using an internal or external clock (not shown) so that it may further provide control of the amount of time in which the heating element 42 is activated and may provide an alarm in the event of a malfunction or in the event of the end of the specified treatment periods. Other function may also be carried out with control processor 160 without departing from the present invention.

FIG. 19 depicts a further embodiment of a mechanism for regulating the temperature of heating element 42. In this embodiment, a control processor similarly controls the operation of the heating element 42 based upon temperature sensed by either a separate temperature sensor 70, or by the heating element 42 itself. This information is used to control a pulse width modulator 168. By increasing the width of the pulses produced by pulse width modulator 168 (i.e., increasing the duty cycle), heating element 42 will produce more heat, and reducing the width of pulses produced by pulse width modulator 168 will reduce the temperature of heat generated by heating element 42. Other modulation schemes, including but not limited to a variable voltage and/or variable current source may also be utilized to regulate the heating of the heater element 42 without departing from the present invention. Again, control processor 160 may also control other functions, as will be discussed later.

Referring now to FIG. 20, the heater unit 80 incorporates (in addition to a thermal heat sink, insulator, back plate, etc.) heating element 42, along with a separate or integral temperature sensor 70 and a vibrating element 136, which all form a part of the heater unit 80 which is placed in contact with the eyelid. In this embodiment, a control processor 160 uses a temperature regulator circuit 172 (such as those previously described or other design) to form a heat regulating circuit 38. Power source 34 supplies power both to the heating element and the control processor 160, as well as to an alarm 176 and vibrator 136. In this embodiment, a user interface 180 (e.g., which may incorporate display 118) is supplied in which the user may interact with the control processor 160 in order to control various aspects of the operation of the device. In one embodiment, for example, the user interface may be utilized to adjust the treatment time. Elements of this and other embodiments may be freely interchanged without departing from the invention.

For purposes of this document, it is useful to define vibratory energy as mechanical motion having a frequency component and amplitude component. It is currently believed to be most desirable that the frequency component be between approximately 0.1 HZ and 300 HZ including random oscillations and that the amplitude component defined as the amount of displacement which is preferably up to about 3 mm, with a currently preferred deflection being about 0.5 mm. However, this should not be considered limiting since optimization of these parameters and definition of a suitable profile may be optimized by experimentation. In one embodiment, for example, the temperature profile might be to establish a constant temperature of 45 degrees C. for 15 minutes with application of linearly increasing vibratory energy from 0.1 HZ to 300 HZ over the last five minutes and the amplitude of the vibratory energy decreasing from 3 mm to 0 mm linearly over the last five minutes. The actual profiles used can be optimized experimentally after considerations of the teachings provided herein.

As noted earlier, the heating profile of the heater element used in prototypes produced a temperature gradient of several degrees Celsius across the eyelid. Prototypes utilized Minco Thermofoil Heater HK5207R6.5L12A. While quite functional, this heater element did not have an ideal temperature profile and thus only heated a portion of the eyelid.

FIG. 21 depicts one example of a heater element design that is customized for heating the eyelid. Such heater element design can be readily custom fabricated by foil heater companies such as Minco of 7300 Commerce Lane, Minneapolis, Minn., 55432. In this embodiment, the outside profile of the heater element is designed to fit the contour of the lower eyelid, but other designs can be devised to treat the upper eyelid or both eyelids simultaneously. One typical set of working dimensions for such a heater design is approximately 1.8 inches for dimension 204, approximately 1.015 inches for dimension 208 and approximately 0.375 inches for the tab 212 at dimensions 214 and 216. Of course, these dimensions should not be considered limiting, but are believed to be suitable for an average sized human eyelid. This design provides tab 212 that is bent back at about 90 degrees away from the eyelid and provides for attachment of wires. Additionally, tab 212 and the shape of the foil heater reduces the unevenness of heating across the eyelid noted in standard commercial foil heaters that were tested.

In accordance with certain embodiments, the heater unit 80, e.g. as in FIG. 20 may be attached with wires and a plug connection to the regulator, so that the heater unit 80 may be detached for cleaning, or for disposal of a portion of (e.g., the heat sink), or the entire heater unit 80. In this manner, sanitation can be maintained while portions of the apparatus can be reused, and speed of treatment enhanced.

The heating is resistive heating produced by the resistance of the conductive path between the conductors that terminate at tab 212. In this embodiment, the heating path meanders left to right and right to left to provide the resistive path producing the heat. In other embodiments, the resistive path can meander up and down and down and up to produce the resistive path as depicted in FIG. 22. Many other patterns can also be used. The dimensions and precise layout of the paths are designed to maintain distance between conductors, line width and resistance appropriate to generate the required heat with an even heating profile, utilizing conventional design principles for foil heater or other resistive heater designs. Moreover, other heating technologies other than foil heaters and other than resistive heating can be used without departing from the present invention.

Those skilled in the art will appreciate upon consideration of the present teachings that many variations in the embodiments depicted are possible without departing from the present invention. For example, the heating element should preferably provide uniform heat across the eyelid, and this may be accomplished using an array of heating elements rather than a single heating element. The heating element is preferably a flexible heating element, such as a foil heating element, to assist with conforming to the shape of the eyelid. However, the heating element may also be rigid and provided in preformed shapes to conform with one average or a variety of eyelid shapes and sizes. Alternatively, a rigid heating element may be accompanied by a soft heatsink which would conform to the eyelid. As discussed earlier this heatsink can be made of a thermally conductive rubber, a fluid, gel or air filled diaphragm a damp cloth or any number of materials which would be thermally conductive and readily conformable.

The heat sink may be made of thermally conductive rubber or silicon or can be an encapsulated fluid or gelatin. In other embodiments, the heat sink can be a solid thermally conductive material which is appropriately shaped to conform to the eyelid geometry (i.e., conform to a surface that is approximately a section of an oblique spheroid). The thermally insulating element 58 can be made from a nonconductive rubber or foam material (where nonconductive is intended to mean low thermal conductivity) or may be made from a low thermal conductivity solid material. The heating element may be used in conjunction with a thermal conductive gel, liquid, or cream to fill gaps between the heat sink and eyelid in order to provide a more uniform conductive boundary between the eyelid and the heater unit. Alternatively, sweat produced from heating the lids inherently assists in increasing heat transfer and is a byproduct using a nonabsorbent heat sink like thermally conductive silicon rubber. The layers depicted can be integrated together in any suitable manner and may take any other form suitable to the end purpose of providing relatively uniform regulated heating of the eyelid.

The regulating element which regulates temperature of the heating element 42 and, if present, the vibratory element 136 may be operated under computer control and may have temperature set points and vibratory set points including amplitude and frequency that are adjustable by the user. Additionally, if desirable, a variety of temperature profiles and/or mechanical energy profiles can be implemented under computer control where the temperature and the vibratory energy can be ramped up and/or down over time if this is deemed to be a desirable control feature. The temperature regulator and/or mechanical energy element can also operate on a timer to limit the time limit of the treatment. While pulse width modulation and simple on/off switching have been disclosed for regulating the temperature of the heating element, other embodiments will occur to those skilled in the art upon consideration of the present teaching. In according with certain embodiments, this heat regulation and/or mechanical energy regulation may be carried out under control of a computer such as a microprocessor operating under control of a computer program stored as instructions in an electronic computer readable storage medium such as a read only memory (ROM) or other suitable storage medium.

The power supply 34 may be based upon batteries which may be replaceable or rechargeable, or the power source may utilize AC power which is converted to DC as needed for implementation of the device.

Any suitable mechanism can be utilized for attaching the heater unit to the eyelid. As disclosed above, this can be done with double stick medical tape or with a head piece, such as goggles, to hold the heater unit in place. In other embodiments, the heating unit may be strapped in place, held in place by the bridge of the nose, swiveled into place, screwed into place by means of a goggle mechanism, latched into placed, or utilizing any other suitable adjustment mechanism from goggles or other head gear. Such mechanism serves to adjust the amount of force placed on the eyelid from the heater unit. In other embodiments, a mechanism may also be devised which automatically adjusts the force placed on the eyelid, and the mechanism may be included either within the heater unit 80 or otherwise coupled to the heater unit 80 (for example, in the goggles) to transmit mechanical energy to the heater unit 80.

Thus, consistent with certain embodiments, an apparatus provides regulated heat to at least one of a patient's eyelids, using a heater unit having a heating element that produces heat that is transferred to the patient's eyelid when electrical signal is applied thereto. A temperature regulator applies an electrical signal to the heating elements in order to achieve heating of the heating elements to a specified temperature range.

Figure 23:
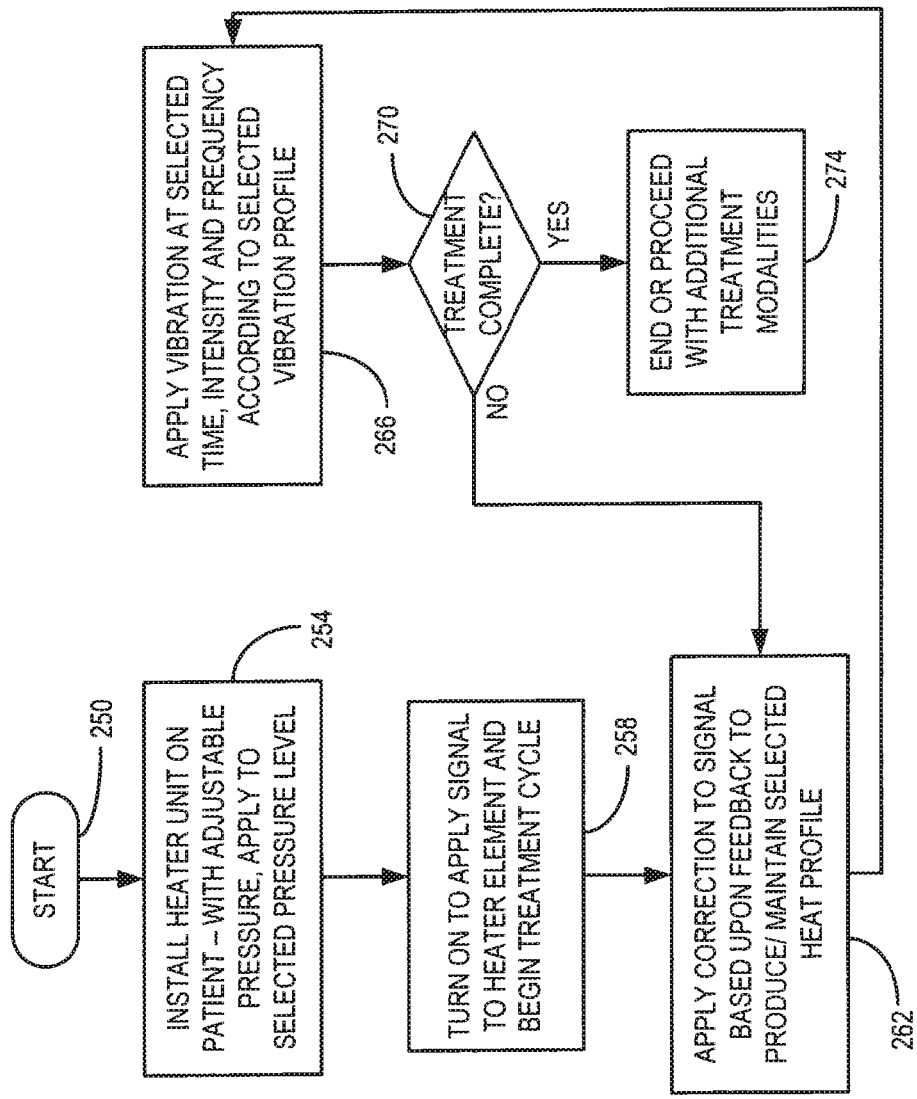
FIG. 23 is a flow chart of a treatment process consistent with certain embodiments of the present invention.

With reference to FIG. 23, one can envision any number of treatment regimens that can be carried out using the various embodiments disclosed. This flow chart depicts the general process one would go through to carry out a treatment in accordance with certain embodiments starting at 250. At 254, the heater unit is installed onto the patient (e.g., using the goggle arrangement or adhesive arrangements depicted). In those embodiments in which pressure can be applied, the pressure is adjusted to urge the heater unit into contact with the eyelid or eyelids to be treated with a selected measure of gentle force. The heater unit can then be turned on and the treatment cycle begins according to a manual or automated process at 258.

Once the heater unit reaches an appropriate treatment temperature (e.g., 45 degrees C.), feedback control is utilized to maintain the heat at a constant level or to achieve a desired heat treatment profile at 262. Similarly, at a desired timing of the treatment profile, mechanical energy can be added (if the embodiment of the heater unit is so equipped) at 266. It currently appears that best results can be achieved when mechanical energy is applied when the therapeutic temperature is reached and discontinued shortly after the heat therapy is completed. This process proceeds according to the selected treatment profile (either selected by an operator or pre-programmed) until the treatment profile is complete at 270. The treatment then either ends at 274 or proceeds with additional treatment modalities (e.g., manual expression).

Thus, a method of treating at least one of a patient's eyelids with a regulated heat in a manner consistent with certain embodiments involves: placing a heating unit having a heating element in contact with the patient's eyelid; and applying a control signal to the heating element to generate heat at the heating element and transfer the generated heat to the eyelid for a prescribed time period.

Referring back to FIG. 8, in use the patient needs only to put on the goggles 98 as one would normally wear swimming goggles and then adjust the set screw (the threaded shaft) until the heater unit comes in contact with the eyelid at a comfortable level of force. At this point, the device is ready for operation and can simply be turned on to begin the treatment. In prototypes and in the preferred implementation, the threaded shaft, back plate, gnarled knob, and other features of the adjustment mechanism are made of nylon and are easily adjustable by the patient, technician, physician, or nurse to apply an appropriate amount of pressure to the eyelid. By placing a small amount of static pressure on the eyelid during treatment, secretions from the meibomian gland are encouraged as the obstruction is dissolved by the heat. In experiments, the amount of pressure used in devices as described in the above-referenced and incorporated by reference applications utilized pulsating pressure ranging up to about 30 $lb/in^2$, with more common ranges being about 2-10 $lb/in^2$. Pulsating pressure can generally be more effective and better tolerated at higher average pressures than an equivalent static pressure. It is therefore anticipated that pressure in the range of up to 2 $lb/in^2$ will be suitable for use as static pressure, with greater pressures being usable in conjunction with other forms of mechanical energy such as vibration, pulsation, and/or milking actions and the like as described above. (For reference, when meibomian glands are manually expressed by squeezing between, e.g., an instrument and a human finger, pressure can reach several hundred pounds per square inch.)

Hence, in the devices disclosed, localized heating of the eyelid only can be obtained so as not to dilate the blood vessels of surrounding facial tissue. When a silicon rubber heat sink is used to transmit heat to the eyelid, a thin layer of sweat develops which appears to enhance heat transfer. The treatment technique is simple and easily implemented and may even be utilized by the patient himself or herself to provide an athome therapy to supplement treatment that may be administered by a medical professional and to assist in keeping the lipids produced in the meibomian glands flowing freely. Since the heat generated is constant or can be regulated to a specified profile, the problems associated with using dry heat, bean bags, or hot, wet compresses are ameliorated. In addition, the device is easily transported, may be operated on batteries if desired, and can be programmed to provide the appropriate amount of heat for the appropriate amount of time.

Additionally, the mess associated with hot compresses and the inconsistent temperature profiles associated with hot compresses and the IR heating approach provided thereby, along with the danger of overheating, is minimized. Since the heating unit 80 is small and lightweight, it can be attached to the eyelid using any of a number of methods depending upon the particular patient and other factors. When attached to the lower eyelid, the device can be used with the eye open. This allows the patient to perform some simple tasks (e.g., reading or watching television) while undergoing treatment in order to pass the time. In addition, the constant pressure applied to the eyelid aids in the excretion of meibomian gland lipids and other fluids as the obstruction is melted. In embodiments utilizing mechanical energy devices, the vibrating, pulsing and or milking action further assists in clearing obstructions.

Those skilled in the art will recognize, upon consideration of the above teachings, that certain of the above exemplary embodiments are based upon use of a programmed processor. However, the invention is not limited to such exemplary embodiments, since other embodiments could be implemented using hardware component equivalents such as special purpose hardware and/or dedicated processors. Similarly, general purpose computers, microprocessor based computers, micro-controllers, optical computers, analog computers, dedicated processors, application specific circuits and/or dedicated hard wired logic may be used to construct alternative equivalent embodiments. It will also be noted by those skilled in the art that certain embodiments may require conversions from the digital to the analog domain and vice versa. Such conversion devices as D/A and A/D converters may be used as required to make such conversions, but are omitted from the drawings for clarity.

Certain embodiments of methods described herein, are or may be implemented using a programmed processor executing programming instructions that are broadly described above, e.g., in flow chart or descriptive form, and that can be stored on any suitable electronic or computer readable storage medium and/or can be transmitted over any suitable electronic communication medium. However, those skilled in the art will appreciate, upon consideration of the present teaching, that the processes described above can be implemented in any number of variations and in many suitable programming languages without departing from embodiments of the present invention. For example, the order of certain operations carried out can often be varied, additional operations can be added or operations can be deleted without departing from certain embodiments of the invention. Error trapping can be added and/or enhanced and variations can be made in user interface and information presentation without departing from certain embodiments of the present invention.

Software and/or firmware embodiments may be implemented using a programmed processor executing programming instructions that in certain instances are broadly described above in flow chart form that can be stored on any suitable electronic or computer readable storage medium (such as, for example, disc storage, Read Only Memory (ROM) devices, Random Access Memory (RAM) devices, network memory devices, optical storage elements, magnetic storage elements, magneto-optical storage elements, flash memory, core memory and/or other equivalent volatile and non-volatile storage technologies) and/or can be transmitted over any suitable electronic communication medium. However, those skilled in the art will appreciate, upon consideration of the present teaching, that the processes described above can be implemented in any number of variations and in many suitable programming languages without departing from embodiments of the present invention. For example, the order of certain operations carried out can often be varied, additional operations can be added or operations can be deleted without departing from certain embodiments of the invention. Error trapping can be added and/or enhanced and variations can be made in user interface and information presentation without departing from certain embodiments of the present invention. Such variations are contemplated and considered equivalent.

While certain illustrative embodiments have been described, it is evident that many alternatives, modifications, permutations and variations will become apparent to those skilled in the art in light of the foregoing description.

What is claimed is:

1. An apparatus to provide heat for treatment of an eyelid, comprising:
   a heater unit comprising:
      an outer insulator layer;
      a central layer comprising at least one heating element; and
      an inner thermal heat sink layer configured to be placed in contact with an outer surface of the eyelid,
      wherein:
         the inner thermal heat sink layer is configured to be affixed directly to the outer surface of the eyelid using an adhesive, and
         the inner thermal heat sink layer is flexible such that when pressed into place on the outer surface of the eyelid, the inner thermal heat sink layer conforms to a shape of the eyelid to provide close contact between the inner thermal heat sink layer and the outer surface of the eyelid;
   a temperature regulator configured to apply an electrical signal to the heater unit,
   wherein the heater unit configured to apply heat directly to the outer surface of the eyelid when an electrical signal is applied to the at least one heating element to heat the outer surface of the eyelid, such that the outer surface of the eyelid is heated to a specified temperature range regulated by the temperature regulator.

2. The apparatus according to claim 1, further comprising a temperature sensor located in the heater unit, the temperature sensor configured to sense a temperature being delivered to the outer surface of the eyelid and provide information relating to the sensed temperature to the temperature regulator.

3. The apparatus according to claim 2, wherein the temperature regulator is configured to regulate an amount of the heat applied to the outer surface of the eyelid based on the information relating to the sensed temperature received from the temperature sensor.

4. The apparatus according to claim 1, wherein the inner thermal heat sink layer is selected from the group consisting of a thermally conductive rubber member, a thermally conductive silicon member, an encapsulated fluid containing member, and a solid conductive member.

5. The apparatus according to claim 1, further comprising a thermally conductive gel, cream, or liquid configured to be placed between the inner thermal heat sink layer and the outer surface of the eyelid to enhance thermal conduction from the inner thermal heat sink to the outer surface of the eyelid.

6. The apparatus according to claim 1, wherein the outer insulator layer is coupled to a surface of the at least one heating element and configured to reduce heat loss from the heater unit in a direction other than a direction toward the outer surface of the eyelid.

7. The apparatus according to claim 6, wherein the outer insulator layer is selected from the group consisting of a non-thermally conductive foam element, a non-thermally conductive rubber element, and a non-thermally conductive solid element.

8. The apparatus according to claim 1, wherein the temperature regulator is further configured to apply a pulse width modulated electrical signal to the heater unit in order to regulate the heat produced thereby.

9. The apparatus according to claim 1, wherein the heater unit has a rigid portion that is configured to directly contact the eyelid, and wherein the rigid portion is pre-shaped to conform to a shape of the eyelid.

10. The apparatus according to claim 1, further comprising a user interface configured to allow a user to establish at least one of the specified temperature range and a specified treatment time that the heat is applied to the outer surface of the eyelid.

11. The apparatus according to claim 1, wherein the specified temperature range is greater than 37° C.

12. The apparatus according to claim 1, wherein the specified temperature range is between 44° C. and 47° C.

13. The apparatus according to claim 10, wherein the specified treatment time is approximately 10 to 60 minutes.

14. The apparatus according to claim 1, further comprising a force generator configured to generate a force on the eyelid to stimulate secretion from at least one meibomian gland in the eyelid.

15. The apparatus according to claim 1, wherein the inner thermal heat sink layer is shaped to approximate a contour of the eyelid and is configured to provide uniform heat across a substantial entirety of the outer surface of the eyelid.

16. The apparatus according to claim 15, wherein the inner thermal heat sink layer comprises at least one flexible heating element having a conductive path that extends substantially across all of a width and all of a length of the eyelid.

* * * * *